United States Patent [19]

Rohrback et al.

[11] Patent Number: 5,254,461
[45] Date of Patent: Oct. 19, 1993

[54] METHOD OF AND APPARATUS FOR DETERMINING MICROORGANISM POPULATIONS ELECTROCHEMICALLY

[75] Inventors: Gilson H. Rohrback, Mill Creek, Wash.; Elmond A. Holmes, Fullerton, Calif.

[73] Assignee: Infometrix, Incorporated, Seattle, Wash.

[21] Appl. No.: 620,528

[22] Filed: Nov. 30, 1990

Related U.S. Application Data

[63] Continuation-in-part of Ser. No. 433,607, Nov. 7, 1989, abandoned.

[51] Int. Cl.$^5$ .............. C12Q 1/04; G01N 25/08
[52] U.S. Cl. .................. 435/34; 435/25; 435/30; 435/32; 435/39; 435/287; 435/291; 436/150; 422/75; 422/76; 422/77; 422/81; 204/1.11
[58] Field of Search .......... 435/34, 25, 30, 32, 435/39, 287, 291; 436/150; 422/75, 76, 77, 81; 204/1.11

[56] References Cited

U.S. PATENT DOCUMENTS

| | | | |
|---|---|---|---|
| 3,228,799 | 1/1966 | Rohrback | 136/100 |
| 3,403,081 | 9/1968 | Rohrback et al. | 204/1 |
| 3,506,544 | 4/1970 | Silverman et al. | 204/1 |
| 3,523,070 | 8/1970 | Silverman et al. | 204/195 |
| 3,526,578 | 9/1970 | Silverman | 204/1 |
| 4,200,493 | 4/1980 | Wilkins et al. | 435/34 |
| 4,246,343 | 1/1981 | Wilkins et al. | 435/32 |
| 4,252,897 | 2/1981 | Axford et al. | 435/34 |
| 4,288,543 | 9/1981 | Sieloff et al. | 435/34 |
| 4,321,322 | 3/1982 | Ahnell | 435/34 |
| 4,386,157 | 5/1983 | Nishioka et al. | 435/39 |
| 4,517,291 | 5/1985 | Seago | 435/14 |
| 4,576,916 | 3/1986 | Lowke et al. | 435/34 |
| 4,614,716 | 9/1986 | Rohrback et al. | 435/39 |
| 4,777,137 | 10/1988 | Lemonnier | 435/34 |
| 4,801,546 | 1/1989 | Ackland | 435/34 |
| 4,983,516 | 1/1991 | Turner et al. | 435/34 |
| 5,089,395 | 2/1992 | Snyder et al. | 435/39 |

OTHER PUBLICATIONS

R. G. Kroll, et al., Jul. 1, 1989, "An oxygen electrode-based assay of catalase activity as a rapid method for estimating the bacterial content of foods", Biological Abstracts, vol. 88, No. 1, (Abstract No. 3556, J. Appl. Bacteriol, 66(3), 209–218 (Eng).

Food Microbiology, vol. 6, No. 3, 1989, USA, pp. 159–169, R. A. Patchett et al. "Rapid detection of bacteria by an amperometric electrode system—a comparison of some redox mediators".

Journal of Applied Bacteriology, vol. 66, No. 1, 1989, Cambridge UK, pp. 49–55, R. A. Patchett et al. "Investigation of a simple amperometric electrode system to rapidly quantify and detect bacteria in foods".

Primary Examiner—Michael G. Wityshyn
Assistant Examiner—Abdel A. Mohamed
Attorney, Agent, or Firm—Richard L. Gausewitz

[57] ABSTRACT

A method of determining populations of live, whole bacteria electrochemically. The bacteria are filtered, and the filtrate is employed in association with an electrochemical measuring unit to determine the bacteria density. In accordance with a flow-through method, the average signal over the predetermined time period of the test is employed, in conjunction with a constant, to determine the population. In accordance with the bypass method, reagent is passed through a bypass line to the electrochemical measuring unit, and the resulting signal is subtracted from the signal resulting from the filtrate, a constant being employed to correlate the resulting remainder with bacteria count. A changing-concentration method employs a changing concentration of bacteria in the same fluid to determine populations of bacteria. A saved-sample method employs a second test of the same filtrate, after a predetermined time period, to compensate for any contaminants that may be present. Additional major embodiments relate to use of potential measurement to achieve the electrochemical measuring, to the measurement of rate of change of potential; and to a gas method of rapidly obtaining undiluted filtrate.

16 Claims, 5 Drawing Sheets

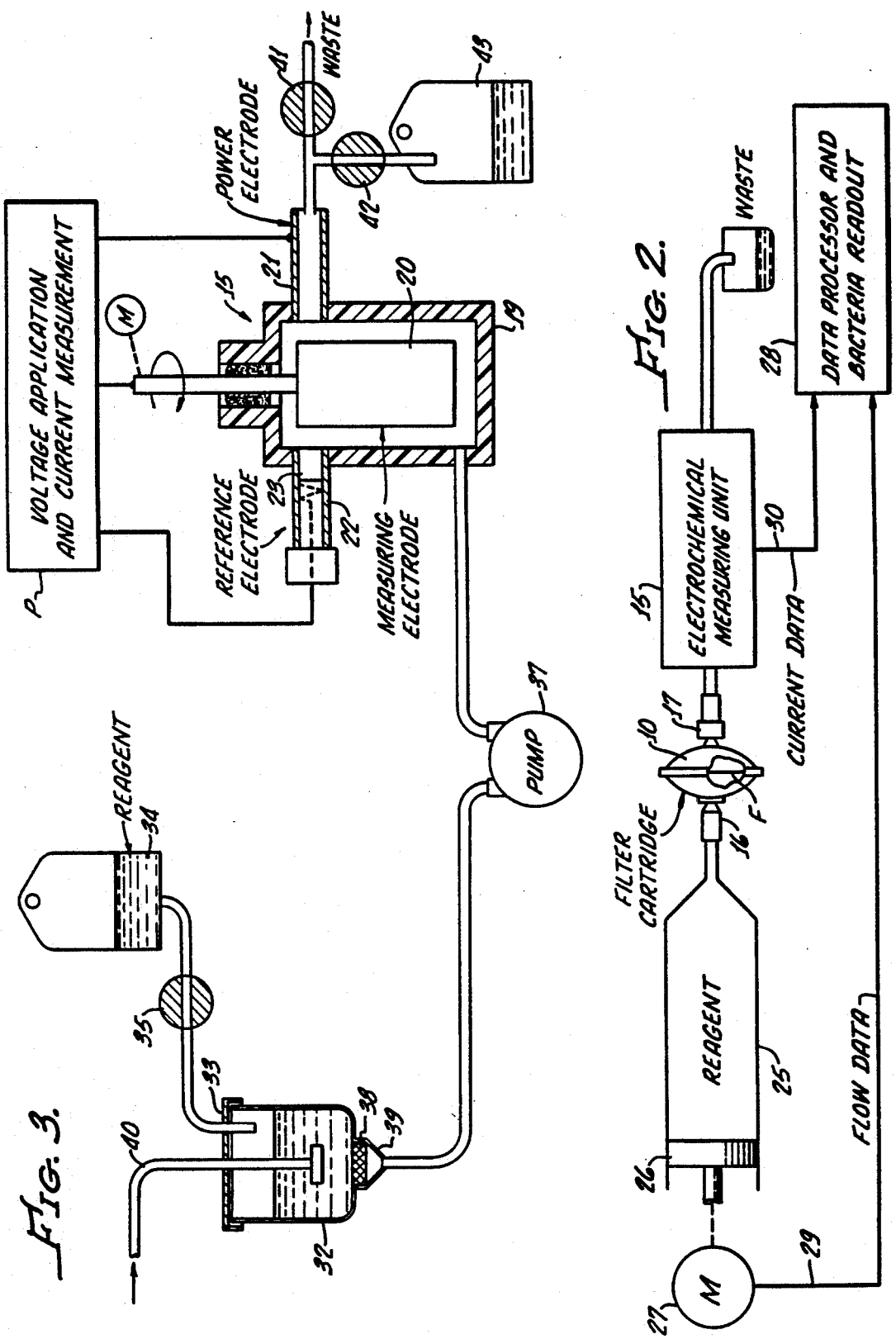

METHOD OF AND APPARATUS FOR DETERMINING MICROORGANISM POPULATIONS ELECTROCHEMICALLY

CROSS-REFERENCE TO RELATED APPLICATION

This application is a continuation-in-part of co-pending patent application Ser. No. 433,607, filed Nov. 7, 1989, now abandoned, for Methods of Determining Bacteria Populations Electrochemically, inventors Gilson H. Rohrback and Elmond A. Holmes.

PRIOR ART AND ITS LIMITATIONS

Over a period of decades, various electrochemical methods have been proposed for determination of populations of bacteria. A basic method is disclosed in U.S. Pat. No. 3,506,544, entitled, "Method of Determining Microbial Populations, Enzyme Activities, and Substrate Concentrations by Electrochemical Analysis", inventors H. P. Silverman and J. M Brake. Said Pat. No. 3,506,544 is hereby incorporated by reference herein.

The cited Silverman/Brake patent describes a two-step reaction process by which: first, a bacteria or enzyme-catalyzed oxidation/reduction reaction occurred, and second, an electrochemical oxidation reaction of the reduced species (reduced form, state or substance), that was produced in the first step, was carried out to produce a measurable current. Stated more specifically, the bacteria or enzyme sample was mixed with a special water-based reagent which contained both a suitable substrate and the oxidized species of an oxidation/reduction (redox) couple. This reagent/sample mixture was placed in a vessel containing a three electrode system, namely a power electrode, a reference electrode, and a current-measuring electrode. A control and measuring system (a) maintained the measuring electrode at a selected potential relative to the reference electrode, (b) caused the reduced redox species produced by the bacterial or enzyme action to be oxidized back to its higher oxidation state, and (c) measured the current resulting from this electrochemical reaction.

Because the enzymatic-activated reaction (first step) occurred throughout the entire fluid volume, whereas the electrochemical reaction (second step) occurred only at the surface of the measuring electrode, it was assumed that the depletion of the enzyme-produced reduced species by the electrochemical reaction was negligible compared to the build-up of concentration of the reduced species. Therefore, the concentration of the reduced species continually increased and the electrochemically produced current increased proportionately. It was "key" to the Silverman/Brake process that it was the rate of increase of the electrochemically produced current which was determined. Except for important variations and problems, this rate of current increase was proportional to the rate of increase in the concentration of the reduced species, which in turn was proportional to the rate of the enzyme catalyzed reaction, which was proportional to the concentration of the bacteria or enzyme in the original sample.

Thus, the indicated electrochemical method of prior art was to determine bacteria concentration by measuring a current that was related to the sample, and computing the bacteria population density by using the assumed relationship:

$$\text{Bacteria} = K \frac{dI}{dT}$$

K was a calibration factor (or proportionality factor). The prior art assumed that this K was constant, but applicants believe that in many instances it was not actually constant.

In addition to the major limitation of the prior art relative to the lack of constancy of the calibration or proportionality factor, there were other serious drawbacks of prior art systems. These include the following:

(1) Many bacteria species have a propensity to attach themselves to surfaces, and may even find surfaces having impressed potentials (as on electrodes) particularly attractive sites for establishing colonies. Accordingly, in prior systems the electrodes which were exposed directly to bacteria samples needed to be cleaned and sterilized after each test. This was a time consuming and expensive task. Single use, disposable electrodes were developed but these were too expensive, causing test costs to become excessive. Even more troublesome was the action of the bacteria on the measuring electrode. The bacteria could alter the characteristics of this electrode and cause its electrochemical activity to change significantly, even during the period of a test. Stated otherwise, part of the difficulty in prior art systems was caused by changes in the activity of the measuring electrode relative to the electroactive substance in the fluid, and by changes in the effective area of such electrode.

(2) There were important problems relative to contaminants. In the context of the present patent application, a contaminant is defined as any substance in the original test sample (other than the bacteria themselves) which will produce a current at the measuring electrode. This may result from a contaminant promoting the reaction in the above-mentioned "first step" (generally this contaminant is a free enzyme which came from the bacteria prior to commencement of the test). This may also (or alternatively) result if the contaminant is a substance which will itself be directly oxidized at the measuring electrode at the potential value used. Either action will produce a spurious current and an incorrect bacteria count. In addition to the basic problem of having a contaminant present in the sample, often there is also a variation in contaminant concentration from sample to sample and thus a variation in the current caused by the contaminant. An exactly constant contaminant current from sample to sample, from a given system, would be compensated for in the calibration factor derived from independent plate counts of the sample. But this is rarely the case.

(3) Many prior inventors working in the field of electrochemical measurement of bacteria population have not realized that care must be taken to prevent damage to the bacteria by mechanical abuse. If bacteria are subjected to sufficient mechanical stress, their membranes may be ruptured, releasing a vast number of enzymes which will markedly alter the catalytic ability of the solution to produce the reduced species of the redox couple (first step). Even seemingly mild disturbances can produce significant effects on the bacteria. It is believed by applicants that the rapidly spinning, rotating electrodes generally used in prior systems may rupture bacteria membranes, as would other abrasive or destructive mechanical methods that have been used.

(4) Another characteristic of the prior art was that there was often widely fluctuating current. Such fluctuating current made it difficult to interpret results, or to be sure of the bacteria count.

The various drawbacks of the prior art were such that electrochemical systems for determining populations of bacteria have not proved to be of major practical value and have not had major commercial importance. This was especially true relative to tests to determine small populations of bacteria.

General Objects of the Present Invention

Objects of the present invention include (without limitation) the following: (a) Assuring that the bacteria will not be subjected during the test procedures to harsh mechanical treatment which could rupture their cell membranes and thus produce free enzymes, and will not be subjected to less violent disturbances which could alter the bacteria's ability to catalyze a chemical reaction. (b) Making electrochemical measurements without any bacterial contamination of electrode surfaces. (c) Determining or compensating for that portion of the current measure which is caused by background or by any contaminant present in the sample. (d) Making an initial reduction in the amount of contaminant in the original sample, thereby producing a "purified" sample before testing. (e) Achieving accurately, relatively rapidly, and practically, the bacteria count densities desired by many companies, scientists, and professionals.

The above and other objects are achieved in several ways. These will now be described.

Additional general objects are stated, much later in this specification, under the subheading "Discussions, Statement of Further Objects of the Invention, Additional Summary of the Invention, and Additional Written Disclosure, Added by the Continuation-in-Part Application"

SUMMARY OF THE INVENTION

The first new and improved method employs a filter cartridge which has collected the bacteria (or other microorganism) from the sample to be counted. A reagent fluid is moved through such cartridge while an electrochemical measurement of the reduced species caused by the bacteria is made in the filtrate from the cartridge. The bacteria count is then determined as a function of the fluid flow, electrochemical signal, and time. It is emphasized that (in accordance with one major aspect of the invention) the procedure is such as to make the direct response of the electrochemical signal a characteristic to the bacteria while nulling the contaminant.

The second new and improved method comprises moving the fluid sample from a vessel through a filter while electrochemically measuring the reduced species caused in the filtrate stream and then determining the bacteria count as a function of changing bacteria concentration, electrochemical signal, and time. An important aspect of this method is that the procedure is such as to make the second derivative of the electrochemical signal characteristic to bacteria while nulling the contaminant.

In accordance with one major aspect of the present invention, the electrochemical measurements are performed in the filtrate, without the presence of bacteria, as distinguished from measurements made in a chamber containing both fluid and bacteria. Because the measurements are made in the filtrate, there can be no mechanical abuse of the bacteria at the measuring electrode or elsewhere. Furthermore, there is no possibility of bacterial contamination of the measuring electrode or of other parts of the apparatus beyond the filter. Stated in another manner, applicants have discovered that marked improvements are achieved by placing the entire electrode assembly in the filtrate, such filtrate having been produced either by a filter cartridge, which has previously been used to collect bacteria from the original sample, or by a filter positioned at or downstream from the outlet of a vessel containing the bacteria.

The "electrochemical" measurement of reduced species, as referred to herein, includes the standard procedures for electrochemical measurement, including measure of electrode current at constant potential, and/or electrode potential at constant current, and/or other voltametric or amperometric methods to determine the concentration of an electrochemically active substance.

The measuring electrode may be made from a variety of chemically inert and electrically conductive materials, such as platinum, palladium, gold, carbon, graphite, etc., and in any of many standard configurations such as rotating, stationary, capillary, rods, wire, etc. In a two electrode instrumentation, the reference and power electrodes may be combined to be a standard type of reversible electrode used both to sense potential and to supply current. The three electrode system contains a measuring electrode, a reference electrode, and a power electrode; whereas a four electrode system comprises a measuring electrode, a power electrode and two reference electrodes.

There are different forms of the aspect of the present invention by which the electrochemical measurements are made in the filtrate, and each form has variations. In accordance with one method, bacteria are collected in a filter cartridge at a test site, and the cartridge is then taken to a laboratory where the bacteria count density is determined The determination is effected by passing a reagent solution into and through the bacteria-containing filter cartridge, in such manner that bacteria present in the cartridge will cause the production of substantial reduced species in the filtrate. The reagent, with its reduced species, then flows to the electrochemical measuring unit, where the current produced by electrochemical action generated by the reduced species is determined. This current is adjusted for contaminants, for background current, and for electrochemical unit calibration, to produce the bacteria count density of the original sample.

The average flow rate of reagent solution through the filter cartridge is caused to be sufficiently low that the bacteria will produce significant reduced species. Preferably, instead of using a constant flow rate, the method is so performed that there is intermittent flow. This is done by causing the flow rate to be zero for a predetermined period of time, and then using a specific flow rate for a period of time, with electrochemical measurements being made during the entire procedure.

To amplify upon portions of the above, and to state additional aspects of the invention, reagent is introduced into a container--very preferably a small-volume filter cartridge--which contains the bacteria from a predetermined volume of original sample. The reagent is held in the cartridge for a predetermined time period which is sufficiently long that any bacteria therein will cause the production of sufficient reduced species to generate measurable current in the electrochemical measuring unit. Then, the reagent is passed out of the cartridge to the electrochemical measuring unit, and a measurement is made in the filtrate. Furthermore, the same reagent, but reagent which was not introduced into the cartridge, is passed to the electrochemical measuring unit independently of the cartridge. Another measurement is made relative to this second-mentioned reagent. The difference between the measurements is multiplied by a calibrating constant, such constant having been determined by an independent method on an aliquot of the original sample. Later, the procedure is repeated relative to other samples, and using the same steps as those stated, using the previously-determined constant.

In another form of the method, the reagent is passed through the bacteria-containing cartridge at different low flow rates, and measurements are made in the electrochemical measuring unit relative to each rate. The effects of background are thus compensated.

A further method of determining bacteria count density normally makes use of much larger volumes than do the above-indicated "cartridge" methods. The original sample (preferably a purified sample created by prefiltering) is placed in a vessel containing a filter at the chamber exit path. After a period of environmental adjustment for the bacteria in the chamber, during which period reduced species is produced, the reduced species is drawn from the chamber and passed through the electrochemical measuring unit. Measurements are made relative to two substantially different concentrations of bacteria in the (one and the same) fluid. These measurements are then employed to determine bacteria population, there being no errors introduced because of the presence of any contaminants in the fluid. Very preferably, the two different concentrations are achieved by filtering liquid out of the above-indicated vessel, the electrochemical measurements then being made in the filtrates In accordance with an additional form, the determination of bacteria count involves saving part of the fluid after it is filtered and made the subject of a measurement in the electrochemical measuring unit. Later, the electrical signal produced by the saved filtrate is determined and is compared to the signal it first produced in the original pass through the electrochemical unit. It is then known whether or not contaminant is present, and a correction is made relative to the measured bacteria count.

Additional summary of the invention is stated following the subhead which appears much later in this specification, and reads as follows "Discussions, Statement of Further Objects of the Invention, Additional Summary of the Invention, and Additional Written Disclosure, Added by the Continuation-in-Part Application". Said summary is hereby incorporated by reference into the material written under the present subheading.

DESCRIPTION OF THE DRAWINGS

FIG. 2 is a schematic or diagrammatic view of apparatus for performing what may be called the flow through method of the present invention;

FIG. 3 is a schematic or diagrammatic view of apparatus for performing what may be called the changing-concentration and saved-sample methods of the present invention;

FORMING OF A PURIFIED SAMPLE

Figure 1:
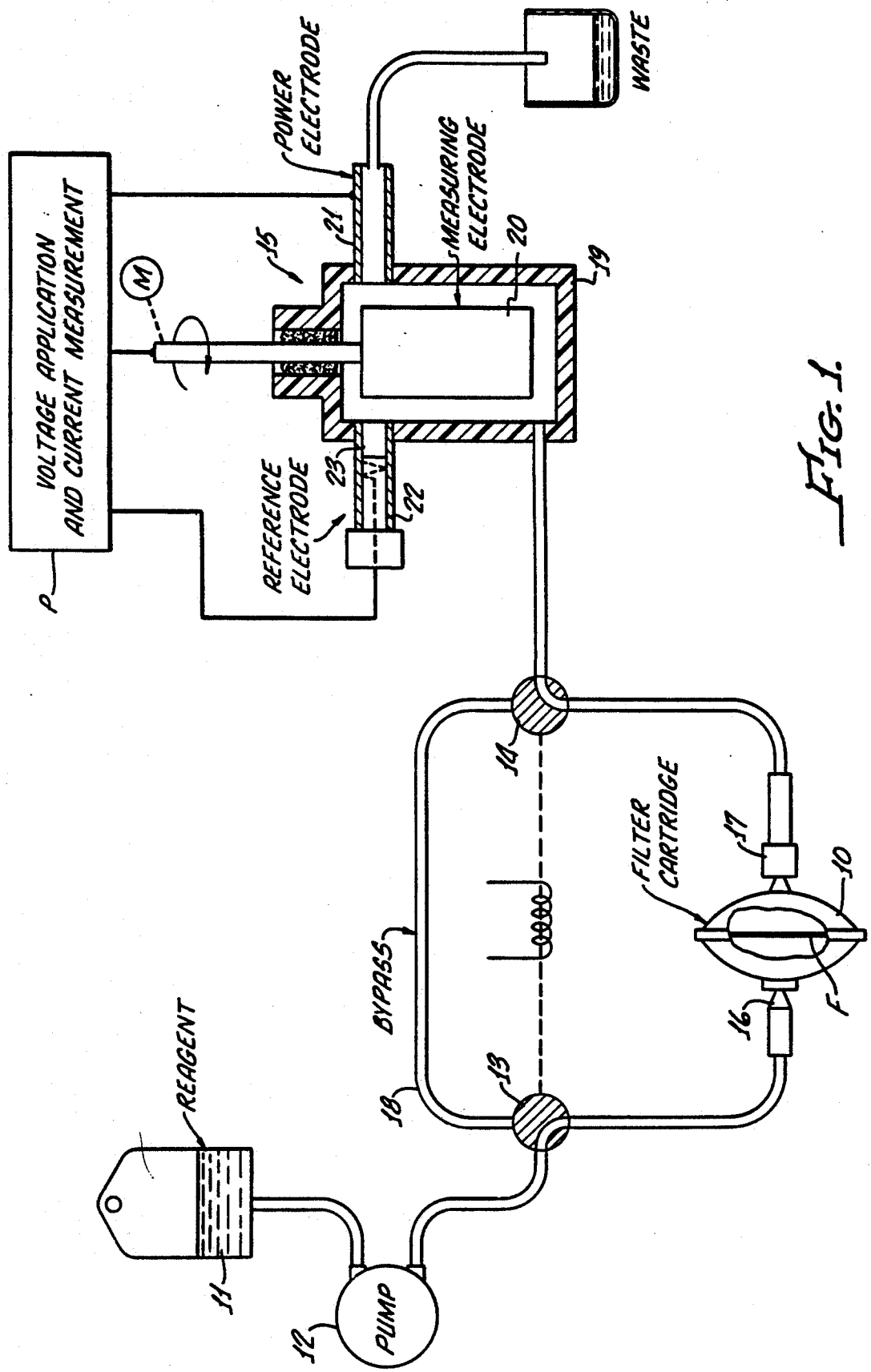
FIG. 1 is a schematic or diagrammatic view of apparatus for performing what may be called the bypass method of the present invention, a central region of the filter housing being broken away to show the filter.

Throughout this specification and claims, unless the words "coarse filter" are used, the word "filter" means micro filter. This is one of the many commercially available micro filters which are suitable to retain bacteria in filtration. These filters are sterile and neutral biologically, being neither cytotoxic, bactereostatic nor bactericidal.

It is preferred to perform, separately, an initial filtration step before the below-described methods are commenced. This is because of the vast quantities and types of contaminants that are present in many industrial systems. For example, commercial oxidants are commonly used for bacteria and algae control. Chlorine, chlorine dioxide and acrolein are all electrochemically active and will affect the electrochemical signals produced by the electrochemical measuring unit. Many other biocides, herbicides, and algecides will introduce errors, as will various water conditioning agents.

Even when chemical treating agents are not present in the original sample, free enzymes will normally be present. These will have been formed from the bacteria themselves through the normal process of excretion of enzymes by the bacteria through their membrane walls. The presence of these enzymes, which are contaminants, will cause a high reading of bacteria count density A purified sample is preferably made by, first, passing the raw sample through a coarse filter, then discarding the coarse filter, thereafter filtering again (by a micro filter) the filtrate that passed through the coarse filter, and collecting the bacteria on such second-mentioned filter The raw filtrate that results from such procedure is discarded, and below-described procedures are commenced.

It is emphasized that the bacteria are kept alive and uninjured. Thus, for example, they are not allowed to become dry on a filter, and they are not subjected to mechanical or other abuse. After initial filtration, a purified sample is made by taking the filtered original sample, washing it, and reconstituting it with reagent fluid.

A purified sample may in many cases be made by use of the reagent itself, without the separate steps stated in the preceding paragraphs.

A filter cartridge may be positioned at an appropriate point in a commercial plant, for example at a test spigot A predetermined volume of fluid from the plant is passed through the spigot and filter cartridge. Then, the cartridge is filled with reagent fluid so as to keep the bacteria alive, following which the cartridge is plugged at each end. The cartridge is taken to a test laboratory where the present method is performed, or the method may be performed at the plant itself.

As a specific example, milk at a dairy may be passed through a spigot having a coarse filter therein, and subsequently flowed slowly through a filter cartridge. Then, after a suitable predetermined amount of such flow, the cartridge is removed and taken back to the test laboratory for testing to determine bacteria count density.

Detailed Description of the Bypass Method

As an aid to description of what may be termed the bypass method, there will first be described, with reference to schematic or diagrammatic FIG. 1, an apparatus for use in performing that method. It is, however, pointed out that although the apparatus of FIG. 1 measures current, other electrochemical signals (such as potential) may also be measured. Preferably, though not necessarily, the bypass method makes use of a filter cartridge such as is indicated at 10. This is a small-volume closed container across which is extended, in sealing relationship, a filter F typically formed of synthetic resin and adapted to prevent passage of bacteria while permitting passage of liquid. An exemplary volume of the cartridge is of the order of 1 cc.

Flow through the filter is typically slow, for example 1 cc, or less, per minute. It is to be understood that the conduits that connect to the filter cartridge 10 and to other components are preferably small in internal diameter, so that even the stated slow flow through the filter cartridge 10 does not result in excessive time periods for passage of filtrate to the electrochemical measuring unit.

A bag (or other container) 11 of reagent connects through conduits to a pump 12 and thus to one component 13 of a double pole-double throw valve. The other component 14 of such valve is connected to the first component 13, for example by solenoid means, so that both components 13,14 work simultaneously.

When the valve components 13,14 are each in one position, reagent from bag 11 passes through pump 12 and component 13 to filter cartridge 10, thence to valve component 14 and on to the electrochemical measuring unit 15. It is to be understood that the filter cartridge is connected in series with valve components 13,14 by couplings 16,17 that permit removal of the cartridge from the system when desired, and permit mounting of a new cartridge when desired A bypass 18 connects between valve components 13,14 to conduct reagent therebetween independently of the cartridge 10. When the valve components 13,14 are each in the other position, reagent flows from bag 11 and pump 12 through the bypass 18 to measuring unit 15.

The illustrated electrochemical measuring unit 15 has an insulating housing 19 in which is mounted a measuring electrode 20. The measuring electrode shown here is a cylindrical carbon electrode that is rotated slowly in housing 19, by motor M, and is in relatively close-fit relationship in the housing. Suitable seals prevent leakage. The volume of the chamber within the housing (exteriorly of the electrode) is small, preferably less than 1 cc.

The electrochemical measuring unit further comprises a power electrode 21 and a reference electrode 22, the latter being substantially isolated from the chamber around measuring electrode 20 as by a conductive plug 23. The measuring, power and reference electrodes are connected to terminals of a voltage application and current measuring apparatus P well known in the art, one example being described in the above cited Pat. No. 3,506,544. A picoammeter, not shown, is provided in apparatus P to measure current flow in the measuring electrode.

It is to be understood that the reference electrode 22 maintains a substantially constant potential, and monitors the potential of the measuring electrode which can thereby be itself maintained at a substantially constant and selected potential. This is done by means of an appropriate circuit and by application of current from the power electrode 21 to the measuring electrode.

In the illustrated electrochemical measuring unit 15, fluid from housing 19 passes out through the power electrode 21 to waste.

Proceeding next to a description of the method, this comprises passing reagent through a filter on the upstream face of which are collected (from a known volume of original sample) a known bacteria the population of which is to be determined. (The type of bacteria is known either from experience in the particular industrial system, etc., or by microscopic or other analysis.) The bacteria are washed to remove contaminants, either prior to connection of the cartridge in the circuit (as described above), or by the first amount of flow of reagent through the filter.

At least during a desired time period after such washing of contaminant from the bacteria, the pump 12 is so operated that the average flow of reagent through filter cartridge 10 is sufficiently low that the bacteria in the cartridge will generate sufficient reduced species that a measurable current will be generated in the electrochemical measuring unit 15.

Stated more definitely, a known volume of original sample is passed through the filter cartridge 10, either at an industrial plant or in the laboratory. This results in collection of bacteria on the upstream face of the filter F in the cartridge. Then, the cartridge is filled with suitable fluid and is placed in circuit by couplings 16,17, with the bacteria on the upstream face of filter F. Pump 12 and the valve components 13,14 are then operated to pump reagent from bag 11 alternately through filter cartridge 10 and bypass 18, the manner of flow and rate of flow through the filter cartridge being repeatable (and repeated) for different samples.

The electrochemical measuring unit 15 is used to make current measurements, preferably at all times, and the amplitudes of the currents are compared In other words, the bypass-caused current is compared to the cartridge-caused current. Thus, when the conditions are such that the fluid in the electrochemical measuring unit is from the cartridge, the current will be relatively high because of the effect produced by the bacteria. On the other hand, when the fluid in the electrochemical measuring unit is from the bypass 18, and which has not passed through the cartridge, the current will be relatively low because it is background current, current not representative of bacterial action in the cartridge.

When the amplitudes of the currents measured by the picoammeter repeat, the test may be terminated. Stated otherwise, when the same current amplitudes are produced each time the fluid is from the cartridge, and the same (lower) current amplitudes are produced each time the fluid is from the bypass, the test may be terminated. Furthermore, only one reading need be made relative to fluid from the cartridge, and one relative to fluid from the bypass, provided the prior testing for a given system has been performed sufficiently that it is known the results will repeat should the alternate readings be continued.

(The word "amplitude", as used in this specification, can mean peak, integral, least mean square, etc., so long as the same definition is employed from test to test; any variations thus introduced are then part of the constant indicated below.)

The method further comprises subtracting the current generated when the fluid in the electrochemical measuring unit came from the bypass, from the current generated when the fluid came from the filter cartridge. This current difference is then multiplied by a constant or proportionality factor ($K_1$) to thus read out the bacteria count density in colony forming units (cfu's) per milliliter, in the original sample. This constant ($K_1$) is one which correlates the bacteria count determined by the present method, when the procedure is repeated from sample to sample, with a count made by an independent means (for example, a plate count) on an aliquot of the original sample.

If the current read (by the picoammeter) on each occasion when the fluid in the electrochemical measuring unit is from the bypass is highly constant from reading to reading, then picoammeter readings occurring when the fluid is from the cartridge—and even though such picoammeter readings are only small amounts larger than the readings when the liquid is from the bypass—are significant. On the other hand, when the "bypass" readings vary slightly, it is desired that the test be so performed that the "cartridge" readings be greatly higher than is the case relative to the "bypass" readings. In the latter situation, it is often desirable that the "cartridge" readings be caused to be at least two or three times the variations in the "bypass" readings.

The present bypass method, with intermittent flow, is one best mode contemplated by the inventors at the time of filing the original (parent) application.

A constant or intermittent flow rate through the cartridge may be employed at all times when the valve 13,14 is in such position that reagent from pump 12 passes through the cartridge, depending (of course) on whether the pump is on or off. When the valve 13,14 is shifted so that it passes reagent through the bypass 18 instead of through the cartridge, flow through the cartridge is zero.

The length of time the valve 13,14 is switched to bypass position, so that there is no flow through cartridge 10, is preferably changed in a known manner—from sample to sample—that is related to the expected (or determined in the early stages of the test) bacteria count. Thus, if the bacteria count is low, then the length of time that the reagent is caused to remain in the cartridge 10, without flowing, is caused to be relatively long. If, on the other hand, the bacteria count is expected to be high, the length of time the reagent is caused to remain in the cartridge 10 is caused to be relatively short. In both cases, the period is such that the bacteria generate sufficient reduced species to cause the electrochemical measuring unit to make a significant and meaningful measurement.

There are different constants to correlate the current readings with the bacteria count density. For example, there is one constant for a three-minute period of zero flow in the cartridge, and another constant for a nine-minute period of zero flow in the cartridge. Both of these constants are such that both the nine-minute and three-minute periods will produce the correct bacteria count density readout. Both constants are determined, as stated above, by correlating the current readings after they are repeatable again and again, with bacteria count densities determined by (for example) a plate count of the same volume of sample.

It is to be understood that pump 12 is preferably stopped when the system is in "bypass" condition, as soon as fluid from the bypass has reached the electrochemical measuring unit and purged it of filtrate from the cartridge. This condition is known to exist as soon as the picoammeter reads minimum current. Conversely, when the system is in the "cartridge" condition, it is know that filtrate has purged the electrochemical measuring unit of reagent from the bypass, because the picoammeter will then show a maximum reading.

The specific electrochemical method described above uses the measurement of current as the output signal for determination of bacteria population, but the method is not limited thereto. Any other method suitable for determination of reduced species, such as a method employing potentiometric instrumentation, may be substituted.

In many applications it is preferred that a data processor be employed, as stated under the following subhead.

Detailed Description of the Flow-Through Method

The flow-through method comprises moving a reagent through a filter cartridge (or other container) containing the sample of bacteria, namely the bacteria from a predetermined volume of original sample, and measuring the reduced species in the stream of filtrate. Two sets of data, namely fluid flow versus time, and currents indicating reduced species versus time, are used in data processing to determine the bacteria count density.

The flow-through method is the other best mode contemplated by the inventors at the time of filing the original (parent) application.

Referring to FIG. 2, there is shown one form of apparatus for use in performing the flow-through method. The electrochemical measuring unit 15 is identical to the unit 15 described relative to FIG. 1. As in FIG. 1, the filter cartridge 10 is connected to the unit 15, the cartridge being removable because of the presence of the couplings 16 and 17. In FIG. 2, the reagent pump is illustrated as being a syringe 25 the piston 26 of which is driven by a motor 27. Motor 27 is associated with sensing or other means that sense motor and/or piston positions, and that transmit flow data to a data processing and bacteria readout unit indicated schematically at 28. Unit 28 is also fed current data from the measuring electrode. The transmission of flow data to unit 28 is indicated by the arrow 29, while the transmission of current data thereto is indicated by the arrow 30. It is to be understood that the voltage application and current measurement unit P, indicated relative to FIG. 1, is also present in the apparatus of FIG. 2 either directly or by equivalency. For example, the box labeled "electrochemical measuring unit" in FIG. 2 may also incorporate the "voltage application and current measurement" box of FIG. 1. Alternatively, for example, the picoameter may be provided in the data process block 28.

When there is a constant flow rate of reagent through the filter F in cartridge 10, that is to say when motor 27 is operated at a constant speed, the bacteria count density will be equal to a constant times the average current sensed by electrochemical measuring unit 15 and transmitted to the data processing unit 28. Such a steady flow rate may be employed where the concentration of bacteria is quite high, or where the pump is operated so as to create a very slow flow (distinctly slower than in the below-stated example under the present subheading).

In a preferred form of the flow-through method, determination of bacteria count is effected by making measurements at two different flow rates through the cartridge.

Whether the flow is constant, intermittent or variable, it is repeated from test to test relative to different samples. Furthermore, all conditions are kept the same from test to test. Then, for each type of test, that is to say for each computer program (where flows are determined by computer), a constant ($K_2$) is known which correlates the average current with the actual bacteria count density This constant is derived, for each type of test, by (for example) making a plate count. Then, for a later test (in all embodiments of the invention), the same constant is employed time after time.

When the flow through the filter in the cartridge is caused to be zero for a predetermined time period, there will an accumulation of reduced species in the cartridge 10. Then, when the flow is started at the end of the predetermined time period, the flow will move the thus-accumulated reduced species to and into the electrochemical measuring unit 15. The integral of the current generated in the unit 15 will be the area under the current pulse (a curve of current versus time) that results from the transmission of the specified accumulation to the unit 15. When the flow program is exactly repeatable and is repeated from sample to sample, there is a constant proportion between the amplitude of the pulse and the area under the curve (generated, for example, in the data processor 28). Therefore, the bacteria count density is equal to a constant times the current, where the current is the amplitude of the pulse resulting in the unit 15 because of the presence of the accumulation received from the cartridge.

A radical difference between the present flow-through method and prior art is that the flow-through method does not measure a rate of change of current, in order to determine bacteria population. Instead, the present flow-through method measures the average current flowing at the measuring electrode at a constant average flow rate.

In accordance with one aspect of a preferred form of the flow-through method, reagent is passed through the filter in cartridge 10 at a rate so fast that very little reduced species is generated, especially if the bacteria density is low. It follows that the vast majority of liquid passed to the electrochemical measuring unit from the filter is then only reagent, not reduced species. The resulting current transmitted to the data processor is properly regarded as background current.

To state an example of the flow-through method, let it be assumed that the size of the filter is such that the first pulse of reagent (having a volume of 1 cc, and a flow rate of, for example, 1 cc/minute) washes the great majority of residual contaminant out of the filter cartridge. Then, a second pulse, also 1 cc at 1 cc/minute, produces the background current. Again, this assumes that the bacteria count density in the cartridge is sufficiently low that the 1 cc/minute produces very little reduced species Thereafter, after these first two pulses, the pump is stopped and there is caused to be a delay of, for example, fifteen minutes. Then, after the delay, the pump is again started to effect flow through the filter at the rate of 1 cc/minute. This propels the pulse, slug or volume of filtrate to the electrochemical measuring unit 15. The current indicated by the picoammeter or the data processor 28 then shows when such pulse containing substantial reduced species begins to enter the unit 15; the signal thereafter produced is related to the concentration of reduced species. When such slug has passed through the measuring unit, the signal returns to essentially the same background current as previously measured (this being the base line). The bacteria count is then equal to a constant ($K_2$) times the average amplitude of current produced by held slug, less the background current. The bacteria count density can be read out by the data processor, for example in colony forming units per milliliter (cfu's/milliliter) of original sample.

The present method comprehends making current measurements at two different fluid flow rates. Such two flow rates effectively provide the means for electrical measurement of two different bacteria concentrations in one and the same fluid, this being because the effect of bacteria concentration in a filter cartridge is inversely proportional to the flow rate. The relationships are such that the effect of contaminants is nulled out in the computed readout of bacteria count.

To state the above in another manner, background current (that resulting from any source other than current produced as a result of bacterial action) is eliminated from the test results if the reagent fluid is moved through the filter cartridge alternately at two different flow rates. The two currents measured in the electrochemical measuring unit, together with the measured flow rates, are used to compute the bacteria count.

Applicants have found that the component of current ("I") produced by the bacterial action will be different at the two flow rates ($F_1$ and $F_2$), but the background current component from other sources is substantially constant at all flow rates. Thus, two equations with only two unknowns are provided and solved for B (bacteria):

In general:
$$I_{Measured} = I_{Bacteria} + I_{Background} \text{ (where } I_{Background} \text{ is constant)}$$
Therefore,
at low flow rate $F_1$:
$$I_1 = K_2 \frac{B}{F_1} + I_{Background}$$

at high flow rate $F_2$:
$$I_2 = K_2 \frac{B}{F_2} + I_{Background}$$

Solving for $B$:
$$B = \frac{I_1 - I_2}{K_2(1/F_1 - 1/F_2)}$$

where current values ($I_{1,2}$) and flow rates ($F_{1,2}$) are all measured quantities, and $K_2$ is a proportionality factor derived using an independent method of counting (such as plate count) bacteria in an aliquot of the original sample.

For example, when 1 cc/minute average flow rate causes a 12.1 nanoamp reading, and a 1/10 cc/minute average flow rate causes a 16.8 nanoamp current, $$F_1 = 0.1 \quad I_1 = 16.8$$
$$F_2 = 1.0 \quad I_2 = 12.1$$

then: $B = K_2 \dfrac{(16.8 - 12.1)}{(1/0.1 - 1/1)} = 0.52 K_2$

Detailed Description of the Changing-Concentration Method

The changing-concentration method will be described relative to FIG. 3, which shows one form of apparatus that may be employed in practicing such method. The electrochemical measuring unit 15 in FIG. 3 is shown as being identical to that of FIG. 1, and the same reference numerals are employed relative to it. The same is true of the voltage application and current measurement unit P.

A vessel 32, which in most applications has a volume many times that of the filter cartridge 10, is provided with a vented cap 33. A reagent container 34, for example a bag, connects to vessel 32 through a valve 35. A filter 38 is provided at the bottom of vessel 32, the top face of the filter being preferably in direct communication with the interior of such vessel. Filter 38 is contained in a filter housing 39 which connects to a pump 37, the latter being connected to the housing 19 of measuring electrode 20.

A gas injector 40 introduces an inert and oxygen-free gas into the fluid in vessel 32 in order to remove oxygen from such fluid and in order to stir it. Other elements may be associated with the vessel, for example a mechanical stirrer and a means to introduce washing fluid. The gas passed through the gas injector 40 and thus into the fluid in the vessel preferably comprises oxygen-free nitrogen gas. A sample inlet, not shown, is also provided in the vessel cap or cover 33 in order to eliminate the necessity of removing such cover when sample is introduced.

The liquid that passes through the electrochemical measuring unit goes to waste; it is not recirculated to the vessel 32. Accordingly, a valve 41 is provided in the waste line, and is in open condition during performance of the changing-concentration method.

The changing-concentration method preferably includes the preliminary steps of introducing into vessel 32 a known volume of sample. While valve 35 is maintained closed, the pump 37 is operated so that all liquid is removed from the vessel and passed to waste. Thus, the bacteria in the vessel are present on the upper face of the filter 38.

Pump 37 is then stopped, valve 35 is opened, and reagent is passed from bag 34 into vessel 32 to fill it to a desired level. Valve 35 is then closed. The gas injection means 40, alone or in combination with a mechanical stirrer, is employed to purge the reagent of oxygen and (preferably) keep the reagent-bacteria mixture homogeneous. The apparatus is now ready to commence testing for bacteria count.

Stated generally, the basic concept of the changing-concentration method is to change the concentration of bacteria in one and the same liquid (by removing fluid from vessel 32 via the filter), and to measure the rate of increase in concentration of reduced species (by means of a suitable electrochemical measuring unit). There are thus generated two sets of data, one being concentration of reduced species versus time, and the other being concentration of bacteria versus time. These data are used to determine bacteria count per unit volume, there being a nulling of the effects of any contaminants that may remain after washing. Any one of a large number of concentration programs (procedures) may be employed, and each has its own data processing algorithm which uses the two sets of data in a function that is characteristic to bacteria.

The preferred method of concentration of bacteria employs filtering, as shown in FIG. 3. Pump 37 is started to reduce the volume of bacteria-containing reagent in vessel 32 from an initial volume (which may be termed $V_1$) to a substantially smaller volume (which may be termed $V_2$). At predetermined times, for example when the volume of liquid in vessel 32 is $V_1$ and (subsequently) when the volume is $V_2$, the electrochemical measuring unit 15 is employed to read the electrochemical signal at each concentration. Preferably, electrical signals are transmitted to a data processor from the electrochemical measuring unit, and volume signals are transmitted to such processor from the pump 37 or from sensors associated with vessel 32.

In the preferred form of the changing-concentration method, a data processor is employed and is fed signals from the electrochemical measuring unit and from the pump or vessel, so as to receive inputs of volume versus time and signal versus time. The pump 37 is caused to commence operating shortly after reagent is introduced into vessel 32 from the reagent container 34, and the electrochemical measuring unit is caused to continuously measure current while the pump is operating.

Then, the data processor is caused to determine the second derivative of the signal present in the measuring electrode 20. Such second derivative is proportional to the bacteria count (B). If the signal is a current measure, the general equation is:

$$B = \frac{K_3 d^2 I}{dt^2}$$

B is the bacteria count; $K_3$ is a proportionality constant which is derived (in the manner described above) by using a plate count, etc.; and I is the current in the measuring electrode.

Any desired flow program may be employed, but the program must be repeated from sample to sample. As before, all conditions must be maintained the same from test to test.

A second method of converting the readings produced by the measuring electrode in the changing-concentration method to bacteria count density is a follows. Pump 37 is started, and three currents are measured by the electrochemical measuring unit, the currents being measured equally spaced in time. Specifically, at volume $V_1$, current $I_1$ is measured. Then, more fluid is passed from the vessel 32 to cause a volume $V_2$ to be present. Current $I_2$ is then measured. At a time interval equal to that recorded between the $I_1$ and $I_2$, and while the volume remains at $V_2$, measurement of current $I_3$ is made.

The bacteria count (B) is then determined by the following equation:

$$B = K_4(I_4 + I_2 = 2I_3)$$

As before, the constant $K_4$ is one which was determined in accordance with an independent counting method, such as plate count, so as to translate the results of the equation to the actual bacteria count density in cfu/milliliter.

The above-described changing-concentration method eliminates the effect of any residual contaminants. It is pointed out that although the concentration of bacteria in the reagent increases as reagent is filtered from the bottom of the vessel and pumped to waste, there is no corresponding increase in the concentration of contaminants. The concentration of contaminants remains the same while the concentration of bacteria increases. Thus, mathematically, the contaminants may be eliminated from the equations so that only the effects produced by the bacteria are employed to produce the bacteria count density.

Detailed Description of the Saved-Sample Method

Referring again to FIG. 3, the apparatus employed in the saved-sample method may be substantially the same as that described above relative to the changing-concentration method. However, a valve 42 is provided in a Tee that extends to a container (such as a bag) indicated by the reference numeral 43.

The saved sample method greatly reduces or eliminates the effect of any residual contaminants in the bacteria (remaining after preparation of the purified sample as set forth above), in the following manner.

The first part of the method is the same as that described above relative to the changing-concentration method. However, the liquid that passes through the electrochemical measuring unit during the test (during which readings are made by the electrochemical measuring unit) is not passed to waste but instead to the bag 43, the valve 42 being open and valve 41 being closed. Furthermore, during passage of the filtrate and reagent from filter housing 39 through pump 37 and the electrochemical measuring unit to valve 42, measurements are made by the electrochemical measuring unit.

Thereafter, at a substantially later time, the saved sample of liquid is again passed through the electrochemical measuring unit. This may be done, for example, by separating the bag 43 from the conduit associated with valve 42 and introducing the saved sample from such bag into pump 37 and thus to the electrochemical measuring unit. The introducing is done by means, not shown, independently of vessel 32. The saved sample is then made the subject of second current measurements.

It is thus determined whether or not contaminant was present when the original reading was made. A second-pass current signal equal to the originally measured current demonstrates that no contaminant was present. On the other hand, an increased current relative to the saved sample of fluid indicates the presence of a contaminant. In the latter event, the quantity of any such current increase is employed as a correction factor. Stated otherwise, the difference between the current resulting from the second pass of liquid, and the current resulting from the original pass of liquid, is computed. This difference is subtracted from the current measured when the liquid was originally passed through the electrochemical measuring unit. Then, the thus-corrected current is employed to determine the bacteria count density. (The results are employed in conjunction with a constant, determined by plate count, to achieve the density.) The test is repeated again, in identical manner, from sample to sample.

Specific examples

Example 1

Enzyme test to show viability of bypass method

Enzymes from cryptic soy broth are known to catalyze the reaction between certain oxidants and substrates, including methylene blue and glucose. This characteristic was used to test the viability of the bypass method, by determining current response to the buildup of reduced species (in this case reduced methylene blue).

A small plastic container with a volume of about ½ ml was charged with a 50/50 mixture of reagent and cryptic soy broth. The cartridge had input and exit connections so that it could be used in the bypass apparatus as a substitute for the filter cartridge (FIG. 1). The small container was placed in the test loop, and a waiting period of 15 minutes was selected to allow catalytic action by the enzymes to form a concentration of reduced methylene blue. The reagent had the following composition:

| | |
|---|---|
| $H_2O$ | 75 ml |
| mono basic phosphate | 0.4 g |
| $K_2HPO_4$ | 0.8 g |
| glucose | 0.14 g |
| methylene blue | 0.005 g |
| potassium chloride | 0.35 g |

The tryptic soy broth had the composition:

| | |
|---|---|
| $H_2O$ | 100 ml |
| pancreatic digest of casein | 1.7 g |
| papaic digest of soybean meal | 0.3 g |
| NaCl | 0.5 |
| $K_2HPO_4$ | 0.25 g |
| dextrose | 0.25 g |

During the last minute of waiting period, the reagent was moved by the pump through the bypass, into the electrochemical measuring unit, and the current zeroed (caused to appear to be zero, even though background current was flowing). At the end of the waiting period, the reagent flow was shifted from the bypass route to flow through the container holding the reagent/soy broth mixture. When the slug of retained liquid, held in the plastic container was passed through the electrochemical measuring unit, a peak current (over zeroed background or base line) of 120 nanoamperes was recorded, which subsequently returned close to the zeroed value when the slug had passed. This test confirms that when a reduced species is formed by biological action, the concentration of reduced species can be measured easily by the peak current produced in the electrochemical measuring unit.

Example 2

Quantitative bacteria test of the bypass method

In this test, a syringe filter from the Nalge Company (of Rochester, N.Y.) was used to retain the bacteria. The sterile filter membrane of cellulose acetate was 25 mm in diameter and had a pore size of 0.45 microns. The top of the filter was removed and a new top added, which increased the volume of the space above the filter surface to about ½ ml A pure culture of E. coli bacteria (about 1 ml) was filtered through the filter membrane. The filter cartridge was then filled with the methylene blue/reagent fluid used in Example (1) above, and the cartridge was placed in the apparatus loop as shown in FIG. 1 A holding period of 15 minutes, after introduction of the reagent, was employed.

As in Example (1), near the end of the retention period, the reagent was moved via the bypass and through the electro-chemical measuring unit where the current was zeroed. Then the reagent flow was shifted to pass through the filter cartridge. When the slug of retained fluid reached the electrochemical measuring unit, a peak current of 4.5 nanoamps was observed Moving the retained slug out of the cartridge resulted in fresh reagent entering the filter cartridge. This was held again for a period of 15 minutes, and the determination of the change in current was repeated as above. A peak current of 4.6 nanoamps was recorded, which showed that for a specific waiting period the concentration of reduced species produced (as measured by the electrochemical measuring unit) was essentially constant.

The fresh reagent solution, which now occupied the filter chamber, was again held, this time for a period of 30 minutes. A determination of the peak current for this holding period was found to be 9.4 nanoamps, essentially twice the current found for the 15 minute holding periods. This test showed that the quantity of reduced species which is produced is proportional to the time held in the filter chamber. The slight increase in peak current over the expected value of 9.2 (2×4.6) may be a result of the increase in the total number of bacteria that occurred during the hour period required to carry out the three tests on the same bacteria sample in the cartridge.

Example 3

Qualitative tests with different microorganisms and different reagent compositions.

Two additional tests were made to determine if a peak current was produced by the pulse mode of the bypass method when there were present bacteria other than E. Coli, and with a reagent having a different oxidant and substrate:

| Conditions | Example (1) | Example (2) |
|---|---|---|
| Micro organic: | Yeast | B Globigii |
| Oxidant: | Phenazine Methosulfate | Methylene Blue |
| Substrate: | D-Glucose | Sodium Succinate |
| Buffer: | Phosphate | Phosphate |

The tests, in each case, showed a readily measurable peak current after a 15 minute holding period.

The present invention has created the ability to measure the concentration of reduced species with an accuracy and sensitivity that now makes electrochemical measurement practical and useful. The preferred method directly measures the magnitude of the electric current produced in an electrochemical measuring unit, as opposed to the prior-art method of measuring the rate of change of produced current. Further, the invention completely compensates the current measurement for background contribution from the reagent, contaminants and electronic noise. This is accomplished by moving a reagent containing the oxidant (oxidized species) and the substrate through the bacteria which are retained in a filter cartridge, and then through an electrochemical measuring unit where the magnitude of the current is measured. Subsequently, moving the same reagent through a bypass to the filter cartridge provides a measure of the background current which is subtracted from total current measurement in the filter cartridge flow path to provide the true current component caused only by the bacterial action. This current component has been shown to be proportional to the concentration of the reduced species which in turn has previously been established as being proportional to the bacteria population. Accordingly, it is anticipated that for the new method, bacteria population determined by the independent method of pour plate counting (plate count) will show good correlation with the new electrochemical method of the present invention.

Additional Disclosure

The above-cited Silverman/Brake patent describes such factors as applied voltage, pH, temperature, elimination of oxygen, etc., so these will not be described herein (except for the brief references made above relative to some of these factors). Other factors described in the cited patent, such as relative to the particular substances, etc., are referred to herein only in part because they are already described in the cited patent. Portions of the cited patent particularly referred to herein are those relating to determination of populations of bacteria. However, it is emphasized that applicants present methods are directed primarily toward the determination of populations of live bacteria.

The picoammeter presently employed by applicants is a model 485, manufactured by Keithley Instruments, Inc. of Cleveland, Oh. The filter cartridge presently employed by applicants is catalog number 190-2045, manufactured by Nalge Company, of Rochester, N.Y.

The electrochemical measuring unit now employed by applicants comprises a stainless steel tube 21 as the power electrode. The reference electrode presently employed and now preferred is a silver/silver chloride reference electrode, which may be purchased from many commercial sources. Other reference electrodes, for example the calomel electrode referred to in the cited patent, may also be employed.

The preferred measuring electrode 20 is manufactured by Quantum Electro Development of Fullerton, Calif. This measuring electrode comprises a rotating solid rod of graphite housed in a cylindrical chamber 19 made of polycarbonate, with a clearance between rod and chamber wall of only 0.005 inch. The rod is 1-1/16 inch in length and ½ inch in diameter. The retention volume of the assembly is about ¼ cc. The rod is threaded at its center to receive a stirring rod of 316 stainless steel, which passes through a sealing means to the drive shaft. The driving motor is mounted at one end of the housing chamber. The electrode assembly runs smoothly and with minimal sonic and electrical noise. All of the electrode surfaces are rotated through the fluid at exactly the same speed, and this speed is relatively low in comparison to prior art. The preferred rate of rotation of the electrode is 400 revolutions per minute. (The graphite is obtained from Stackpole Carbon Company of St. Marys, Penna. Specifications are density 1.85, and grade 1336.)

It is emphasized that there are numerous designs of measuring electrodes, including rotation paddles, wire loops, dropping liquid metals, capillary tubes, flat plates, rods, etc. Throw away units have also been employed (as stated above).

Because the present invention employs the step of preventing the bacteria from contacting the measuring electrode, changes in the measuring electrode are much less likely to occur than in prior art. However, it is preferred by applicants that the measuring electrode be tested from time to time Thus, though the measuring electrode is protected from bacterial contamination and from frequent sterilization procedures, there is need for assurance that the measuring electrode activity is correct and constant. The preferred, certain way to provide such assurance is to calibrate the electrode activity occasionally, and to use this calibration in the final calculation of bacteria count. Accordingly, applicants employ means to measure the electrode's sensitivity before and after a test run, or whenever the procedure is deemed to be expedient. Electrochemical unit calibration can be made all-inclusive by determining the actual current measured in the electrochemi-cal measuring unit, which is produced by a known quantity of the particular reduced species which will be measured during a bacteria count. A "standard solution" is used for this test and may be called the electrochemical calibration fluid. The variable area, variable fluid dynamics, and surface activity thereby become combined in one-single calibration factor (with units of current per moles for reduced redox species).

It is emphasized that the electrochemical measuring unit is calibrated by moving a fluid through it, which fluid contains the reduced redox species of known concentration, and measuring the resultant current.

It is also emphasized that the redox (oxidation/reduction) couple is an organic compound that can exist in equilibrium in two states of oxidation and can be changed from one state to the other either by a chemical or electrochemical reaction: for example, the methylene blue/luco methylene blue couple. The oxidized species of the chosen redox couple is present in the reagent fluid. Its function is to assume the role of whatever oxidant normally was used by the bacteria in its natural environment ($O_2$, $SO_4=$, $NO_3-$ or $CO_3=$, etc.). This new oxidant (or mediator) reacts with the substrate (also furnished by the reagent) to produce a new energy cycle for the bacteria.

The new oxidant provided can (a) be used by the bacteria in the energy cycle and (b) produce a reduced species which is easily reoxidized electrochemically. Numerous substances can be used as an oxidant, or there can be cocktail mixtures of two or more. Suitable oxidants can be selected from the well known dye mediators such as methylene blue, 2,6-dichloroindophenol, indigo disulfonate, phenosafranin, phenazine methosulfate, etc. Other substances such as benzoquinone and ferrocyanide have also been found useful.

The substrate is a substance which will combine with the chosen oxidized species of the redox couple in a reaction catalyzed by the bacteria (or its enzyme) to produce the desired reduced species. Many organic substances have been found to be useful in different applications for this purpose. These include the simple sugars such as glucose, lactose, dextrose, fructose, etc., and other intermediate substances in the oxidation cycle, such as pyrunate, succinate malate, citrate, $\alpha$-ketoglutarate, acetate, lactate, etc. As with the oxidized species, a mixed cocktail of two or more substrates can be advantageous.

The reagent is a special solution which supplies the ingredients required by the bacteria for its catalyzed reaction to produce a reduced species. The reagent contains the oxidized state of an organic redox couple (e.g. methylene blue of the redox couple methylene blue/luco methylene blue), a substrate needed for the catalyzed reaction (e.g. glucose), and suitable buffering ingredients to maintain a desired pH level. The reagent is oxygen free and sterile.

Additional general objects are stated under the subheading "Discussions, Statement of Further Objects of the Invention, Additional Summary of the Invention, and Additional Written Disclosure, Added by the Continuation-in-Part Application".

Discussions, Statement of Further Objects of the Invention, Additional Summary of the Invention, and Additional Written Disclosure, Added by the Continuation-in-Part Application The present method and apparatus (described above and below) may be employed to determine the concentrations not only of bacteria but also of other microorganisms.

At the time of filing the continuation-in-part patent application, the preferred (best mode) method of the invention involves the electrochemical measurement of substantially open-circuit potential. Such measurement of open-circuit potential is in combination with other steps set forth above in detail, such as (for example) making the measurement in a filtrate as distinguished from in a liquid containing the microorganisms. At the time of filing this continuation-in-part, the best-mode apparatus, as now contemplated by the inventors, is that described below relative to FIG. 8.

In the above portions of the present patent application, methods are described for determining bacteria (and other microorganism) populations electrochemically. The above descriptive material sets forth in detail the use of current determinations as the electrochemical measurement method, and points out that other electrochemical signals, may be employed. There is described below, in detail, the potential measurement method. More specifically, it is set forth below that using the previously-described bypass method, and substituting potential for current measurement, provides a more sensitive detection of bacteria at low population levels.

The presently-described preferred method involves the use of open-circuit potential, by which is meant substantially open-circuit potential since the system—especially during transient periods—has a small amount of current flowing therein despite the "open-circuit" conditions.

The potential of the reagent that is moved directly from the reagent supply source to the measuring electrode, and the potential of the reagent that was held for a specific period of time in contact with the microorganisms in the filter cartridge, are measured at the same electrode. The difference between these two measured potentials is then employed to determine a proportionality to the microorganism population held in the filter cartridge.

It has been found that the potential at substantially zero current (substantially open-circuit potential) is more stable than is the above-described current at a fixed potential. The potential-measurement method has the advantage of a higher signal to noise ratio. Other advantages of the potential method are markedly increased measuring speed, and the elimination of fluid dynamics factors.

In the potential method, the relationship between concentration of microorganisms (population) and potential is not linear, as was the case relative to the relationship between concentration and current. With the potential method, a non-linear calibration curve is employed to relate the potential measurements to bacteria count. The non-linear calibration curves are often such that low concentrations of microorganisms may be measured very effectively.

In accordance with the preferred form of the potential method, the rate of potential change is employed to determine the electrochemical activity. The rate of change of potential is first measured while bypass reagent is in the measuring electrode, and then is measured again while the reacted reagent is in the measuring electrode. The first-measured potential rate is then substrated from the second-measured potential rate. The resulting signal (the difference between the two measurements) is substantially proportional to or related to the population of the microorganism contained in the filter cartridge The action effected by the microorganism on the oxidant in the reagent causes the oxidant to be consumed, which reduces its concentration. At the same time, the reduced species is produced and therefore increases in concentrations. Both of these concentration changes cause the potential to change, and result in a strong signal response. As was described above relative to the current measurement aspect of the present invention, it has been found that the difference in potential, more specifically (in the preferred form) the difference in rate of change of potential, between the bypass reagent and the reacted reagent can be made proportional to the microorganism count by use of an experimentally determined calibration curve. Such calibration curve is applicable to the exact same system, that is to say same reagent, same volume of raw sample, same electrodes, same time and temperature of incubation in the same filter cartridge, etc.

As with the above-described aspect of the invention by which change in current is employed, many different sizes, shapes and compositions of electrodes may be used to detect differences between the potentials of the bypass reagent and the reacted reagent. It has now been found that the preferred electrode (the measuring electrode) is one having a capillary configuration. As an example, the reagent to be measured is passed through a 1/16 inch hole drilled in a 1 inch rod of inert high-density graphite or inert glassy carbon. Another material that may be employed for the measuring electrode is Ebonite, a conductive titanium oxide. The open-circuit potential of the measuring electrode is measured by comparing it to a commonly used, standard, reference electrode such as Ag/AgCl or Cu/CuSO$_4$. The desired change of potential in the present aspect of the method is determined by passing the bypass reagent and the reacted reagent successively (with the bypass reagent preferably, but not necessarily, being passed through the measuring electrode prior to passing therethrough of the reacted reagent) through the same capillary electrode, and recording the difference in potential between the two reagents.

In a modified system, two identical measuring electrodes may be arranged in parallel. The bypass reagent is then passed through one of these electrodes, and the reacted reagent is passed—at the same time—through the other electrode. The potential difference between the two reagents is then determined without employing a reference electrode.

There has also been found an improved method of moving the reacted reagent out of the filter cartridge and into the electrochemical measuring unit (such unit being composed—in the preferred embodiment—of the measuring and reference electrodes) for potential measurement therein Instead of employing a pump to move the reacted reagent out of the filter cartridge, the present and preferred method involves the injection of gas (preferably an inert gas such as nitrogen or argon) at low pressure (for example, from 5 to 20 psi) into the inlet of the filter cartridge. Such low pressure gas moves all of the liquid out of the filter cartridge (this being the filtrate), but the gas itself does not pass through the filter in the filter cartridge It does not so pass because the micro holes in the filter membrane are so small that the gas does not pass therethrough at the stated pressures This method of ejecting the reacted reagent insures that it moves to and through the measuring electrode without dilution; accordingly, the electrochemical signal produced by the reacted reagent is maximized. The stated method of ejection of the reacted reagent by means of gas provides an improvement of signal resolution as compared to the previously described method of moving the "held" fluid from the filter cartridge by means of a reagent stream.

In the preferred method, in which the time rate of change of potential is measured, the result is obtained in less than a minute. (This does not mean that the entire procedure takes less than a minute, because substantial time is required for "incubation" of the microorganisms in the filter cartridge.) In the preferred method, measurement is made in (for example) about twenty seconds or less.

In the preferred method, the system is not allowed to settle down to some steady-state condition. Although readings of potential rate of change for the first few seconds following introduction of the reacted species into the measuring electrode are disregarded, the readings that then immediately follow are not disregarded but are instead allowed to peak, following which the system is switched to standby. It is this peak which is generally proportional to microorganism concentration. It is the peak rate of change of potential (after subtracting the bypass reagent-produced rate of change) that is so proportional.

The indicated peak reading (after such subtraction) is correlated to microorganism concentration by calibration of the instrument, and by using conventional methods of determining microorganism populations (for example, plate counts). A whole series of different concentrations of fluids that have been held in the cartridge for exactly the same period of time, with exactly the same reagent, the same volume of raw sample, the same temperature, etc., is (as above noted) used to make the calibration curves.

As indicated above, a further important advantage of the preferred potential method, using rate of change, is that the curves can be generally in the nature of log curves. In other words, the response tends to be proportional to the log of the concentration. Accordingly, much better accuracy is achieved, over a wide range of concentrations, than is the case relative to prior systems or even relative to the above-described current embodiment of the present invention.

To state the above in another way, it has been found that the peak potential change or peak rate-of-change signal, after subtracting bypass potential change or rate-of-change signal, is empirically related to microorganism concentration.

Figure 4:
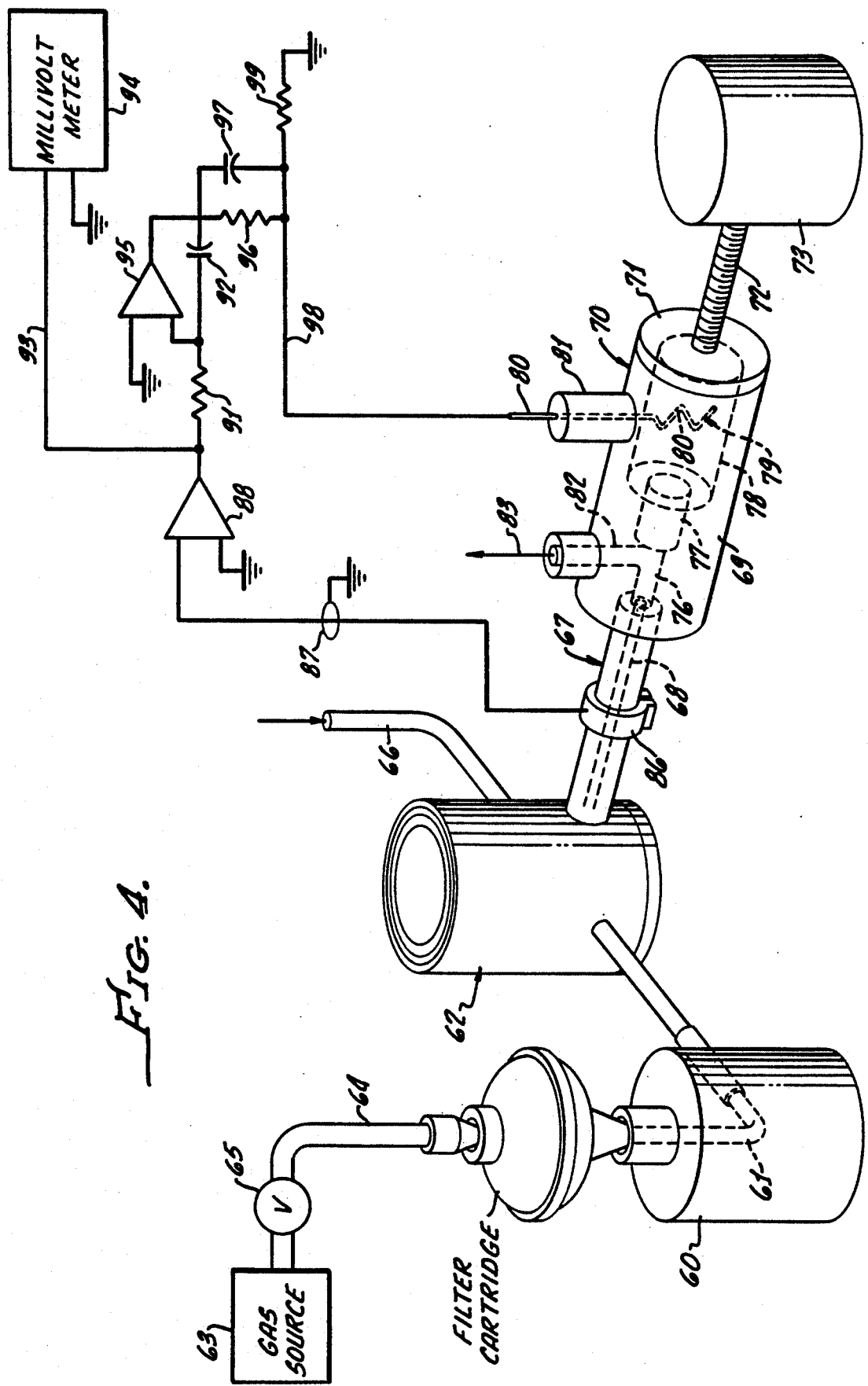
FIG. 4 is a schematic representation, added by the continuation-in-part application, of apparatus for performing the now-preferred embodiment of the method, in which the microorganism population is determined by means of a reading of potential (voltage)

Referring now to FIG. 4, which shows schematically an apparatus which has been employed to perform methods in accordance with the present embodiment of the invention, the illustrated filter cartridge is the same as is shown in FIG. 1 and described relative thereto. Because of the preferred use of gas ejection, the axis of the filter cartridge is preferably vertical as shown.

As described previously herein, the filter cartridge contains microorganisms (such as bacteria) obtained by flowing a certain volume of raw sample (which may have been prefiltered in such a way as not to remove bacteria) through the cartridge, more specifically through the microfilter F (FIG. 1) in such cartridge. The microorganisms are then washed as stated above. Thereafter, also as above described, a sample is reconstituted by injecting into the cartridge a predetermined volume of reagent. The reagent is the same as that described above. There is thus formed the reconstituted sample, which still has the same bacteria that were taken out of the raw sample, but everything else is made in the laboratory or test station.

Preferably, the steps of forming such reconstituted sample are performed by apparatus other than that shown in FIG. 4, following which the cartridge containing bacteria is incorporated into the apparatus of FIG. 4 in the illustrated vertical position (preferably). The upper end of the cartridge is plugged to prevent exposure to the air. Then, the cartridge containing the predetermined volume of reconstituted sample is allowed to stand, for a predetermined time period, in order to form the activated sample (also as stated above).

As above indicated, the time period may vary in accordance with expected bacteria concentration, and may be—for example—two hours.

In the apparatus shown in FIG. 4, the output end of the cartridge (that portion on the side of the cartridge remote from the bacteria, being separated from the bacteria by microfilter F) rests in a cartridge receptacle 60 as shown. The nozzle or connector at the bottom of the cartridge is sealingly connected to a capillary tube 61 which, in turn, connects to a single pole double throw (SPDT) valve 62. One such valve is indicated at 13 in FIG. 1, in section; the exterior of the valve is indicated in FIG. 4. Preferably, the valve 62 is solenoid operated.

A source of pressurized gas, such as (for example) argon or nitrogen at 10 psi, is shown at 63. This connects through a gas line 64 and gas valve 65 to the upper or inlet side of the cartridge, suitable seals being provided to prevent any leakage. This connection is not made, however, until just before performance of the test. Prior thereto, as above stated, the upper end (inlet side) of the cartridge is plugged.

Connected to SPDT valve 62 is a reagent tube 66 for the bypass reagent. This tube is supplied with reagent, such as is described relative to reference numeral 11 in FIG. 1, the reagent flowing either by gravity or through a pump such as pump 12 in FIG. 1. When there is purely gravity flow, in any embodiment of the invention, the pump may be eliminated but the reagent must be at sufficient height to achieve a practical working pressure.

The above-indicated measuring electrode is shown at 67. This, as indicated above under the present subheading, is preferably an inert carbon tube having a small-diameter axial bore through the full length thereof. The bore is shown at 68.

The carbon (or other) measuring electrode 67 has a sufficient outer diameter that 0-rings or other seals may be engaged with both ends thereof, coaxially of and surrounding the ends of the bore 68. One such seal is in a recess in the body of SPDT valve 62, while the other is in a recess in the body 69 of an electrode mounting element 70.

The illustrated mounting element 70 is elongate, being coaxial to the measuring electrode 67, and having a rigid sealing cap 71 at the end thereof remote from the electrode 67. Cap 71 is suitably coaxially associated with O-rings, and is pressed against the end of body 69 by a threaded shaft 72 that extends through an internally-threaded shaft mount 73. Both the shaft mount 73 and the SPDT valve 62 are secured in position as by fasteners connected into a common support, not shown.

When shaft 72 is turned so as to force sealing cap 71 to the left in FIG. 4, the right end of electrode mounting element 70 is closed and sealed and, furthermore, both ends of measuring electrode 67 are pressed into sealing associa-tion with their respective members—namely electrode mounting element 70 and valve 62.

The right end of measuring electrode 67 communicates sealingly with a bore 76 through mounting element 70. Such bore, in turn, communicates with the left end of a porous plug 77 that is mounted in a chamber in electrode mounting element 70. The other end of plug 77 communicates with a chamber, numbered 78, which contains portions of a reference electrode 79. The reference electrode may be of various standard types, as previously indicated. The illustrated type has an aqueous solution and excess wetted solids of silver chloride, and also containing a conductive chloride salt (preferably sodium chloride at a concentration of 0.1M). These are contained in the chamber 78, into which is extended a silver wire 80. The upper portion of the silver wire extends through a mounting boss 81.

The porous plug 77 provides a liquid junction between the liquid in chamber 78 and that in bore 76, while at the same time not permitting flow from bore 76 into chamber 78 or in the opposite direction.

Connecting to bore 76 is a second bore 82 which, in turn, communicates with a tube indicated at 83 that leads to a waste receptacle or drain.

Although the bore 68 in the preferred measuring electrode is small in diameter, namely 1/16 inch in the example, such bore has a relatively large surface area. It follows that the measuring electrode 67 picks up a relatively strong potential signal, the signal to noise ratio being relatively large.

The described apparatus permits simple replacement of the measuring electrode 67 but, to date, it has been found that the described electrode 67 does not rapidly wear out or become ineffective.

An electrically conductive clamp 86 is pressed tightly against the exterior surface of measuring electrode 67, and is connected through a grounded coaxial cable 87 to the input of an operational amplifier 88. The output from amplifier 88 connects to a differentiating circuit composed of a series-connected resistor 91 and capacitor 92. A lead 93 is connected to the junction between amplifier 88 and resistor 91, extending to the input of a millivoltmeter 94.

A second operational amplifier, numbered 95, is connected across capacitor 92, the output of amplifier 95 being connected to that side of capacitor 92 remote from resistor 91. The same side of capacitor 92 is connected through parallel-connected resistor and capacitor elements 96,97 to a lead 98 that extends to the silver wire 80. The output sides of resistor 96 and capacitor 97 are connected through a resistor 99 to ground, it being noted that one terminal of each amplifier 88,95, and one input terminal of meter 94, are also grounded.

The described circuit performs a plurality of functions, one being to differentiate the signal so that the voltmeter 94 senses the rate of change of potential difference between measuring electrode 67 and reference electrode 79. Thus, the voltmeter 94 reads zero when the potential difference between the measuring and reference electrodes is constant. Conversely, the voltmeter 94 reads a relatively large number when the potential difference between the measuring and reference electrodes is changing rapidly. Another function performed by the described circuit is to stabilize the response, and minimize drift. An additional function of the circuit is to amplify the open-circuit potential between reference and measuring electrodes until it may be read by a standard millivoltmeter 94.

The time constant of the differentiating circuit is made quite long, such as twenty seconds or more.

As an example of the specific components employed, amplifiers 88 and 95 are each model AD 548, made by Analog Devices of Norwood, Massachusetts. Resistor 91 has a value of 20 megohms. Capacitor 92 has a value of 1 microfarad. Resistor 96 has a value of 400 kilohms. Capacitor 97 has a value of 30 microfarads. Resistor 99 has a value of 20 kilohms.

The described circuit and component values are given by way of example.

The potential embodiment of the present method will now be described in further detail, with (for convenience) particular reference to the apparatus shown in FIG. 4.

Let it be assumed that the cartridge contains the above-described activated sample (reconstituted), and that such sample has incubated for a desired time period of (for example) two hours.

The operator removes the plug (not shown) from the inlet to the cartridge, and connects thereto the gas line 64. The gas valve 65 is at that time in closed condition.

The SPDT valve 62 is turned to such a position that there is a connection between the bypass reagent tube 66 and the capillary passage 68 in measuring electrode 67. Reagent then flows from the receptacle indicated in FIG. 1, through tube 66 and valve 62 to and through the measuring electrode 67. From there, it flows through passages 76 and 82 to waste tube 83.

Typically, the above-described circuit then reads a certain rate of change in potential between the substrate passing through capillary passage 68 (as sensed by the measuring electrode 67 and associated elements), and the reference electrode 79. However, typically, this rate of change is not great, so the reading of millivoltmeter 94 is then (typically) relatively low.

Before (or while) bypass reagent is passing through measuring electrode 67 as stated, the gas valve 65 is caused to be in open condition so that gas pressure is present on the upper side of microfilter F in the cartridge.

The operator then operates valve 62 to break the connection to reagent tube 66, and substantially simultaneously make a connection between sample fluid tube 61 and the capillary passage 68 in electrode 67.

The reading of millivoltmeter 94 then increases substantially, indicating the rate of change of potential between the measuring and reference electrodes. It is preferred that, for the first five seconds following switchover from reagent to sample fluids, the reading of the meter 94 be ignored. This is because certain instantaneous transients may be present. After the five seconds (in the preferred form), the meter 94 is read until it is determined that the reading has peaked. The peak reading is then noted and recorded, and the valve 62 is shifted back to its original position so that bypass reagent again flows through the capillary passage 68.

Typically, with the described circuit, the meter reading peaks within about twenty seconds after change in the position of valve 62 from reagent to sample.

The gas pressure forces the liquid portion of the activated sample through the microfilter F, but the microorganisms (such as bacteria) do not pass therethrough nor does any gas. This is because of the small size of the pores in the filter F, an exemplary size being 0.45 micrometers.

The sample in the filter cartridge is preferably very small, such as 0.5 cc, 1 cc, or more. The described exemplary bore diameter and length, in the measuring electrode 67, are such that the volume of that bore is only 0.05 cc. The small amount of filtrate is only present in the bore 68 for a short time period, that necessary to achieve a peak reading, following which the position of valve 62 is changed so that reagent again flows through the bore and cleans it. Particularly because no microorganisms are present in bore 68, and because of the short time period, the life of the electrode 67 is relatively long.

The method further comprises subtracting the reading of meter 94 when bypass reagent was present in bore 68 from the peak reading of meter 94 when filtrate was present therein. The difference thus obtained is correlated to a calibration curve as indicated above, to obtain the concentration of microorganisms in the sample.

Tests made on serially diluted samples of microorganisms; relative concentration versus change in potential ($\Delta E$):

The tests show the viability of the potential-measurement aspect of the invention, using microorganisms produced from three different sources: yeast, milk and orange juice. Samples were prepared from each, as follows:

Yeast: About one-half gram of commercial grade dry yeast was added to 500 cc of warm sterile distilled water, stirred and allowed to settle for thirty minutes. A sample of the supernatant liquid was drawn by means of a syringe and used for serial dilution.

Milk: Store bought milk was opened to air and allowed to stand for three days at room temperature. The clear liquid was decanted from the curd and pre-filtered through a 5 mm microfilter paper, which removed the larger biologically inactive particles but left any microorganism present in the raw sample in the filtrate. The filtrate was used to make serial dilution.

Orange Juice: Store bought orange juice was opened to air and allowed to stand for three days at room temperature. The liquid was decanted and prefiltered through a 10 mm microfilter paper, The filtrate which contained any microorganism was used to make serial dilutions.

The original filtrate samples and the samples substantially produced by serial dilution of the three base liquids were tested as follows:

1) 10 cc aliquots of each of the above samples was injected by means of a syringe into special filter cartridges having a 0.45 mm filter pore size and able to hold about one-half cc of liquid above the filter membrane.

2) Each cartridge was then washed with reagent, left filled with reagent and held for a period of four hours at room temperature.

3) The contents of each cartridge after the four hour holding period was moved by gas injection to a capillary measuring electrode (1/16" diameter hole in ¼"×1" rod of graphite) while the potential of the fluid was being monitored.

Figure 5:
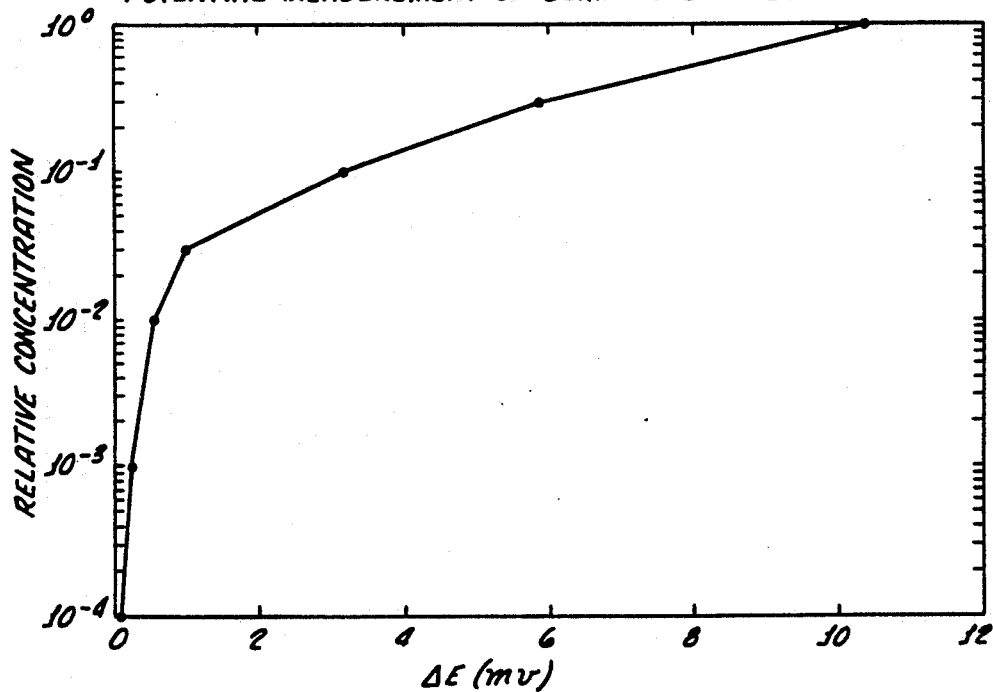
FIGS. 5-7 are curves showing relative concentration of microorganisms versus potential change in relation to serially-diluted yeast, aged milk, and aged orange juice, respectively.
Figure 6:
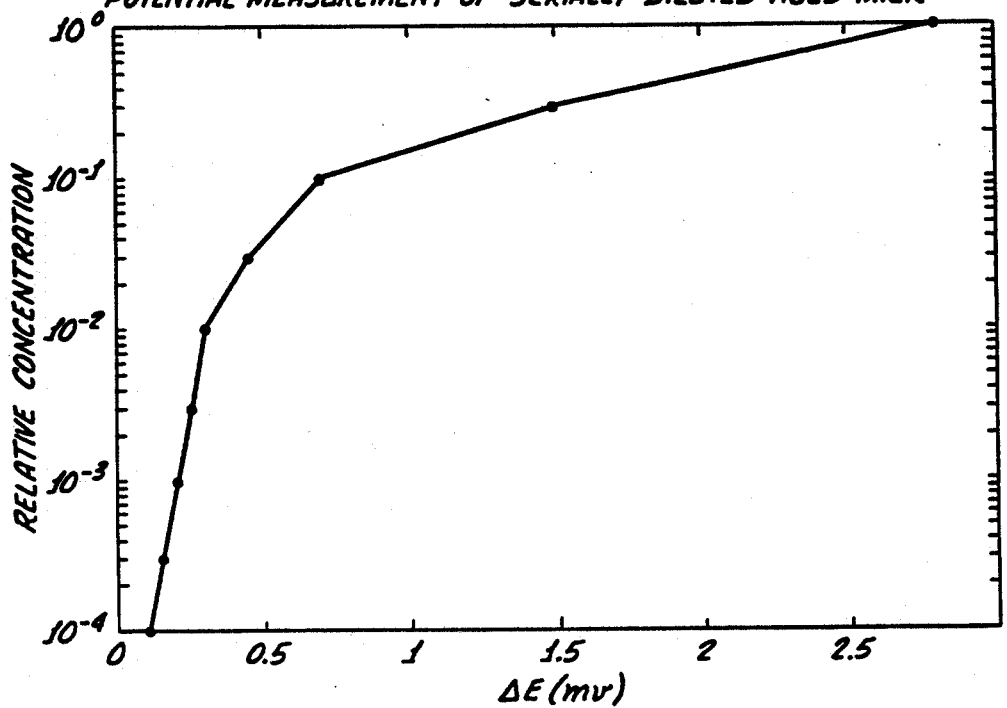
Figure 7:
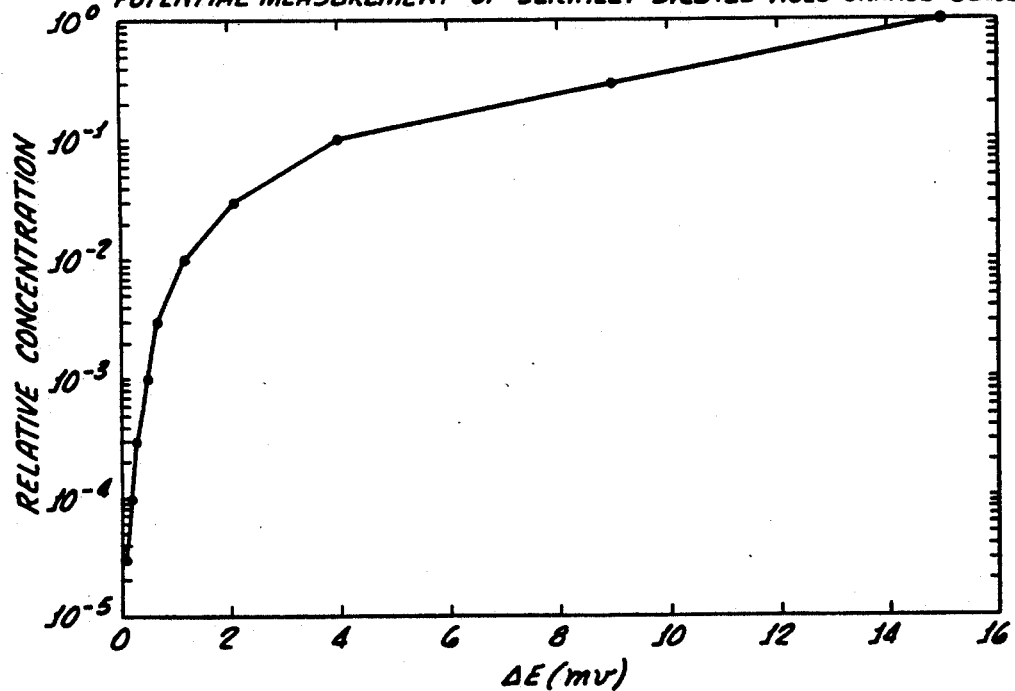

Data from the above-described tests are shown in FIGS. 5-7. These particular tests were run using differences in potential, as distinguished from differences in rate of change of potential. Thus, each point of each curve of FIGS. 5-7 represents a reading determined by subtracting from the potential read by the millivoltmeter, when only the bypass reagent was present in the measuring electrode, from the reading of such meter when active sample was present in such electrode (there having been no differentiating circuit associated with the millivoltmeter).

The plots shown by the three figures demonstrate that the higher the concentration of microorganism, the higher the potential response. They also show the general shape of the calibration curves that are established by using known concentrations to give counts of the microorganisms. The known concentrations are determined by independent methods, such as plate counts of colony forming units (cfu).

Because of the shapes of the curves, the same apparatus may be employed to measure microorganism concentrations in greatly different samples, one of which may have a relatively low concentration and another of which may have a very high concentration. This is, as indicated above, because the illustrated curves are on the general nature of log curves as distinguished from straight lines.

The fungi yeast in the orange juice was primarily saccharmyces cerevisicae. The bacteria in the milk was primarily lactobaccillus dolgaricus. The fungi in the yeast was a mixed species of saccharmyces.

Tests made on known concentrations (by plate count) of microorganisms using change in potential measurement:

Additional tests were run using differences in potential readings, as described above. Two different samples of microorganisms were diluted to give two separate series, comprising three samples of each species. The microorganisms used were a fungi yeast, cultured from orange skins (saccharmyces cerevisiae) and a mold, cultured from apple juice (penicillium, species unknown). Plate counts were determined on the two undiluted samples. All samples were incubated in cartridge filters for three hours at 37 degrees C. The measurements of the change in potential were made as described above. The results are given in the table below, which table indicates the results of the tests made on known concentrations (by plate count) of microorganisms using change in potential measurements.

| Source | Sample | Volume Filtered (ml) | Plate count cfu/ml | Total number microorganisms in filter | Change in potential (millivolts) |
| --- | --- | --- | --- | --- | --- |
| Orange Yeast | 1 | 4.0 | $6.0 \times 10^4$ | $2.4 \times 10^5$ | 2.3 |
| Orange Yeast | 2 | 3.8 | $6.0 \times 10^2$ | $2.4 \times 10^3$ | 0.25 |
| Orange Yeast | 3 | 4.2 | $6.0 \times 10^1$ | $2.4 \times 10^2$ | 0.15 |
| Apple Mold | 1 | 5.0 | $7.25 \times 10^6$ | $3.6 \times 10^7$ | 3.3 |
| Apple Mold | 2 | 5.0 | $7.25 \times 10^4$ | $3.6 \times 10^5$ | 0.45 |
| Apple Mold | 3 | 5.0 | $7.25 \times 10^2$ | $3.6 \times 10^3$ | 0.30 |

It is pointed out that the column entitled "Total Number Microorganisms in Filter" is, in each instance, obtained by multiplying the "Volume Filtered" by the "Plate Count". It is pointed out that for both the Orange Yeast readings, and the Apple Mold readings, the change in potential for the highest number of microorganisms was in each case greater than for lower numbers of microorganisms.

Tests made on known concentrations (by plate count) of microorganisms using rate-of-change of potential measurements:

There are below stated the results of tests that were made using signals related to rate-of-change of potential, as described above. More specifically, as described above, the rate-of-change reading when only reagent was present in the measuring electrode was substracted from the peak rate-of-change reading obtained when microorganisms were present in the measuring electrode.

A pure culture sample of *E-coli* was serially diluted over five decades. The concentration of the undiluted sample was determined by plate count. Each of the serially diluted samples was filtered through a filter cartridge, filled with reagent and incubated for period of three hours at 25 degrees C. The measurement of the rate of change in potential was made as described above; using the preferred apparatus described below with reference to FIG. 8.

| Source | Dilution | Volume through Filter (ml) | Plate count cfu/ml | Total number bacteria in filter | Rate of Change of potential (millivolts) |
| --- | --- | --- | --- | --- | --- |
| 1 | $10^0$ | 5 | $3.0 \times 10^8$ | $1.5 \times 10^9$ | 27 |
| 2 | $10^1$ | 8 | $3.0 \times 10^7$ | $2.4 \times 10^8$ | 11 |
| 3 | $10^2$ | 10 | $3.0 \times 10^6$ | $3.0 \times 10^7$ | 3.9 |
| 4 | $10^3$ | 10 | $3.0 \times 10^5$ | $3.0 \times 10^6$ | 2.0 |
| 5 | $10^4$ | 10 | $3.0 \times 10^4$ | $3.0 \times 10^5$ | 1.2 |
| 6 | $10^5$ | 10 | $3.0 \times 10^3$ | $3.0 \times 10^4$ | 0.9 |

It is to be noted that the numbers in the right column (each of which represents the difference between rate-of-change of potential when only reagent is present and rate-of-change of potential when sample is present) are all empirical as stated above. The signal read is defined by the circuit, and in this case the circuit is that described above relative to FIG. 4.

In the last-stated table, the reagent used was the same as previously described, except that 2,6-dichloroindophenol, at a concentration of $10^{-3}M$, was substituted for the oxidant methylene blue.

The results shown by FIGS. 5, 6 and 7, and by the above two tables, shown that calibration curves will permit population of the microorganism being tested by the described method to be determined by measurement of potential change, or of rate of change of potential.

Figure 8:
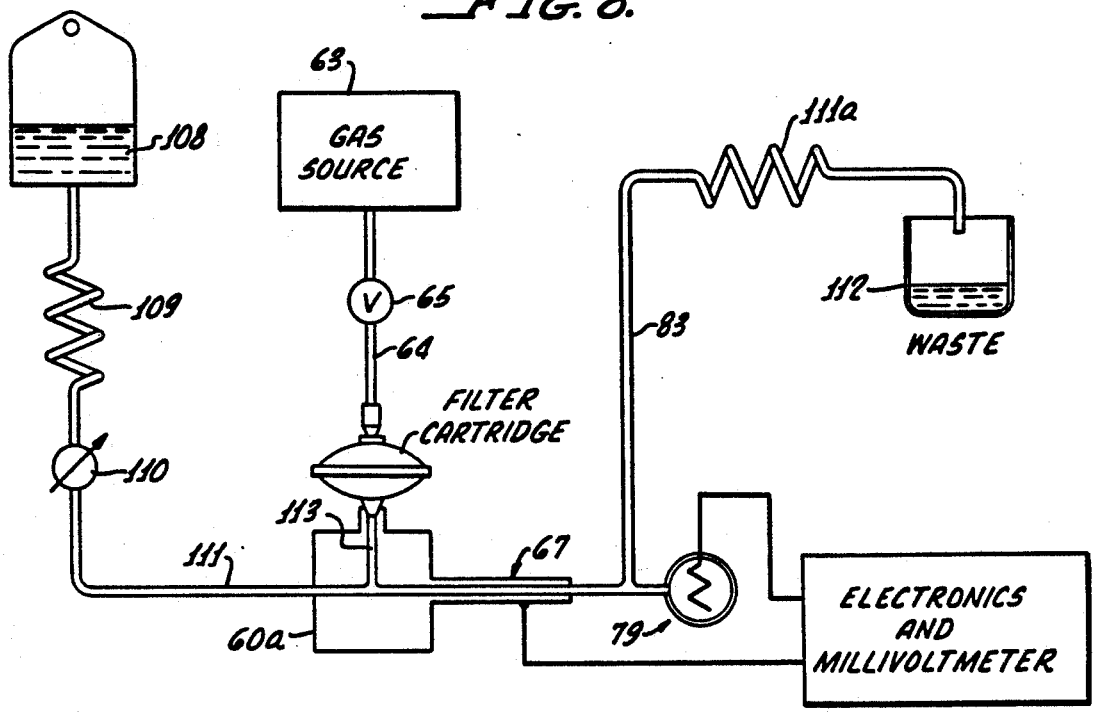
FIG. 8 is a schematic representation of what applicants now consider to be the best mode of apparatus.

In FIG. 8, the electrochemical measuring unit, comprised of reference electrode 79, measuring electrode 67 and associated parts, is the same as described relative to FIG. 4. The box in FIG. 8 labeled "electronics and millivoltmeter" are the same as described relative to the upper-right portion of FIG. 4. The filter cartridge, gas source 63, and gas valve 65 are the same as described relative to FIG. 4.

A bag 108 of reagent is shown at the upper-left in FIG. 8, and feeds by gravity through a restrictor 109 (such as an elongate capillary passage) and a stop cock 110 to a cartridge receptacle 60a. In this embodiment, the SPDT valve is eliminated, with consequent cost savings. The tube or line from bag 108 through restrictor 109, etc., is numbered 111, and extends straight through receptacle holder 60a to the inlet end of measuring electrode 67.

The outlet of electrode 67 flows through the waste line 83 and a second restrictor 111a to a waste receptacle 112. A Tee line or passage 113 extends upwardly from tube or line 111 (within the cartridge holder 60a) to the outlet side of the cartridge.

In the operation of the apparatus shown and described relative to FIG. 8, the cartridge containing the activated sample is present at the upper end of cartridge holder 60a, in sealed communication with line 113. The gas valve 65 is in closed condition. The stop cock 110 is then open. (Such stop cock is merely to prevent dripping between operations, and is not a necessary element.)

Bypass reagent flows by gravity through restrictor 109 and line 111 to and through the measuring electrode 67, thence through line 83 and restrictor 111a to waste receptacle 112. The reagent does not pass upwardly through line 113 and the cartridge, because the valve 65 creates sufficient back pressure to prevent such upward flow, the valve 65 being then in closed condition. A bypass reading is then made by the electronics and millivoltmeter.

Then, all that needs to be done (and is done) is to open the valve 65. The gas pressure forces the fluid portion of the active sample down through line 113 to line 111. Some of the sample flows into and through measuring electrode 67, and other of the sample flows through line 111 toward bag 108. However, the latter flow is sufficiently slow, and the amount of filtrate sufficiently small, that the flow into line 111 is insignificant. On the other hand, there is sufficient sample in measuring electrode 67 to permit making of a sample reading, and one is made by the electronics and millivoltmeter. After gas has ejected fluid from the sample cartridge into 113, 67 and 83, the drip of reagent through line 111 continues but at a rate slow enough to permit measurement of the ejected fluid now contained in the the electrode 67 (it will not be flushed out by the slow drip rate until the measurement is complete). A pneumatic valve (not shown) may be placed in line 111 and activated by pressure in line 64, so that there may be additional measuring time before all of active sample has been pushed out of the electrode. The two (bypass and sample) readings are then compared as described above, and the bacteria count is determined by correlation to a previously-made calibration curve.

The foregoing detailed description is to be clearly understood as given by way of illustration and example only, the spirit and scope of this invention being limited solely by the appended claims.

What is claimed is:

1. A method of electrochemically determining populations of live bacteria, said method comprising:
   filtering a sample of fluid containing live bacteria the population of which is to be measured, to thereby obtain a filtrate,
   wherein said filtering is performed to prevent said bacteria from begin present in said filtrate,
   making an electrochemical measurement relative to said filtrate by employing electrode means contacted only by said filtrate and not contacted by said bacteria, and
   employing the results of said electrochemical measurement to determine the population of bacteria in said sample.

2. The method as claimed in claim 1, in which said method further comprises making said electrochemical measurement by employing an electrochemical measuring unit comprising a measuring electrode, and exposing said measuring electrode of said unit to said filtrate and not to said bacteria.

3. The method as claimed in claim 1, in which said method further comprises (1) washing said bacteria to remove contaminants therefrom, (2) causing said washed bacteria to be present in a reagent comprising the oxidized species of a redox couple, (3) causing said bacteria to catalyze progressive conversion of said oxidized spices to reduced species, (4) filtering said bacteria from said reagent, and (5) employing an electrochemical measuring unit in contact with the filtrate resulting from said preceding step (4), and not in contact with said bacteria, to effect said electrochemical measurement.

4. The method as claimed in claim 1, in which said method further comprises performing said filtering step by means of filter cartridge containing a filter and not containing any electrode.

5. A method of employing an electrochemical measuring unit to determine the population of sieve bacteria in a sample of predetermined volume, said method comprising:
   introducing into a reagent the lieve bacteria to be measured,
      in which said reagent is a fluid comprising the oxidized species of an organic redox couple and a substrate substance usable by said bacteria to induce a catalytic chemical reaction between said oxidized species and said substrate substance to produce the reduced species of said redox couple,
   preventing said bacteria from contacting said electrochemical measuring unit, while causing reduced species catalyzed by he presence of said bacteria to contact said electrochemical measuring unit, and
   employing the resulting signal in said electrochemical measuring unit to determinate the population of bacteria in said sample.

6. A method of electrochemically determining populations of live bacteria, which method comprises:
   collecting a sample of fluid containing live bacteria the population of which is to be measured,
   filtering said sample to obtain a filtrate,
      wherein said filtering is performed to prevent said bacteria from being present in said filtrate,
   making a measurement of potential relative to said filtrate, in such manner that the potential measurement is affected by the composition of said filtrate, and
   employing the results of said potential measurement to determine the population of bacteria in said sample.

7. The method as claimed in claim 6, in which said measurement of potential is made by means of a measuring electrode, a reference electrode, and means to determine the potential difference between said measuring and reference electrodes, and in which said method further comprises causing all of said electrodes to contact only said filtrate, not said fluid sample containing bacteria.

8. The method as claimed in claim 6, in which said method further comprises making said potential measurement by means of a measuring electrode having a capillary passage therein, and causing said filtrate to be present in said passage.

9. The method as claimed in claim 6, in which said potential measurement is effected by measuring the time rate of change of potential, and in which said method further comprises correlating the peak value of said time rate of change to the population of bacteria in said sample.

10. A method of employing electrodes, including a measuring electrode, to determine the population of live bacteria in a sample of predetermined volume, said method comprising:
generating a predetermined-volume sample of the lieve bacteria to be measured,
combining said sample with a reagent,
said reagent being a fluid comprising the oxidized species of an organic redox couple and a substrate substance usable by said bacteria to be measured to induce a catalytic chemical reaction between said oxidized species and said substrate substance to produce the reduced species of said redox couple,
preventing said bacteria from contacting said electrodes while causing bacteria-free reduced species catalyzed by the presence of said bacteria to contact said measuring electrode, said contacting of said bacteria-free reduced species with said measuring electrode generating a potential signal in said measuring electrode, and
employing said potential signal in said measuring electrode to determine the population of bacteria in said sample.

11. The method as claimed in claim 10, in which said method further comprises determining the population of bacteria in said sample by means of apparatus for determining rate of change of said signal said signal said potential signal.

12. A method of determining populations of live bacteria, which method comprises:
collecting a known quantity of a liquid the live bacteria concentration in which is to be determined,
passing said liquid through a coarse filter to remove therefrom any substances the sizes of which are greater than the size of the bacteria whose concentration is to be determined, thereby obtaining a first filtrate
passing said first filtrate through a microfilter to collect on said microfilter the bacteria present in said first filtrate,
washing said thus-collected bacteria in a reagent to remove contaminants from said bacteria,
causing said washed bacteria to be present in a known quantity of said reagent,
passing said last-specified reagent through a microfilter to remove said bacteria therefrom, and to obtain a second filtrate not containing bacteria,
making an electrochemical determination relative to a quantity of said same reagent that has no been exposed to said bacteria, to obtain a first signal,
making an electrochemical determination relative to said second filtrate, to obtain a second signal,
comparing said fist and second signals to each other, and
employing the results of said comparison to determine the concentration of bacteria in said collected known quantity of liquid.

13. The method as claimed in claim 12, in which each of said first and second signals is the rate of change of substantially open-circuit voltage with time.

14. The method as claimed in claim 13, in which said method further comprises making said determinations of rate of change of substantially open-circuit voltage with time, with one determination substantially immediately following the other.

15. A method of determining populations of live bacteria, which method comprises:
collecting a known quantity of a liquid the live bacteria concentration in which it is desired to determine,
passing said liquid through a filter to collect thereon the bacteria present in said known quantity,
causing said bacteria to be present in a first quantity of reagent,
passing said first quantity of reagent through a filter to obtain a filtrate free of said bacteria, and
making an electrochemical determination of the concentration of said bacteria by comparing an electrochemical signal derived from said filtrate to an electrochemical signal derived from a second quantity of said reagent,
said second quantity having a concentration of bacteria different from that in said first quantity.

16. The method as claimed in claim 15, in which said method further comprises making said electrochemical determination over a period of less than one minute.

* * * * *

UNITED STATES PATENT AND TRADEMARK OFFICE
CERTIFICATE OF CORRECTION

PATENT NO. : 5,254,461
DATED : October 19, 1993
INVENTOR(S) : Rohrback et al.

It is certified that error appears in the above-indentified patent and that said Letters Patent is hereby corrected as shown below:

Claim 3 (column 30, line 22), delete "spices" and substitute therefor ---species---.

Claim 5 (column 30, line 33), delete "sieve" and substitute therefor ---live---.

Claim 5 (column 30, line 37), delete "lieve" and substitute therefor ---live---.

Claim 5 (column 30, line 47), delete "he" and substitute therefor ---the---.

Claim 10 (column 31, line 22), delete "lieve" and substitute therefor ---live---.

Signed and Sealed this

Fourth Day of April, 1995

Attest:

BRUCE LEHMAN

Attesting Officer

Commissioner of Patents and Trademarks